United States Patent
Moutte

(10) Patent No.: US 11,364,184 B2
(45) Date of Patent: Jun. 21, 2022

(54) PERFUME COMPOSITIONS

(71) Applicant: GIVAUDAN SA, Vernier (CH)

(72) Inventor: Maxence Moutte, Paris (FR)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 15/744,634

(22) PCT Filed: Jul. 13, 2016

(86) PCT No.: PCT/EP2016/066634
§ 371 (c)(1),
(2) Date: Jan. 12, 2018

(87) PCT Pub. No.: WO2017/012947
PCT Pub. Date: Jan. 26, 2017

(65) Prior Publication Data
US 2018/0193235 A1    Jul. 12, 2018

(30) Foreign Application Priority Data

Jul. 17, 2015   (GB) ..................................... 1512585

(51) Int. Cl.
| | | |
|---|---|---|
| A61K 8/11 | (2006.01) | |
| C11B 9/00 | (2006.01) | |
| A61K 8/25 | (2006.01) | |
| A61K 8/73 | (2006.01) | |
| A61Q 13/00 | (2006.01) | |

(52) U.S. Cl.
CPC .................. *A61K 8/11* (2013.01); *A61K 8/25* (2013.01); *A61K 8/738* (2013.01); *A61Q 13/00* (2013.01); *C11B 9/00* (2013.01); *A61K 2800/48* (2013.01); *A61K 2800/49* (2013.01); *A61K 2800/524* (2013.01); *A61K 2800/59* (2013.01); *A61K 2800/80* (2013.01)

(58) Field of Classification Search
CPC ...................................................... A61K 8/11
See application file for complete search history.

(56) References Cited

U.S. PATENT DOCUMENTS

2014/0194338 A1    7/2014 Behan et al.

FOREIGN PATENT DOCUMENTS

| CN | 1358226 A | 7/2002 |
|---|---|---|
| JP | 2012140555 A | 7/2012 |
| WO | 3066703 A1 | 11/2000 |
| WO | 2010000083 A1 | 1/2010 |
| WO | 2011033047 A1 | 3/2011 |
| WO | 2011141265 A1 | 11/2011 |
| WO | 2011161229 A1 | 12/2011 |
| WO | 2012020076 A1 | 2/2012 |
| WO | 2012069647 A1 | 5/2012 |

OTHER PUBLICATIONS

English Machine Translation of JP2012140555 (A) obtained Jun. 4, 2020 at https://worldwide.espacenet.com/publicationDetails/biblio?CC=JP&NR=2012140555A&KC=A&FT=D&ND=3&date=20120726&DB=EPODOC&locale=en_EP#.*
International Search Report and Written Opinion of the International Searching Authority for corresponding application PCT/EP2016/066634 dated Sep. 16, 2016.
GB Search Report for corresponding application GB1512585.9 dated Jan. 18, 2016.

* cited by examiner

*Primary Examiner* — Arrie L Reuther
(74) *Attorney, Agent, or Firm* — Norris McLaughlin PA

(57) ABSTRACT

A compacted perfume composition comprising at least three Performance Markers A1, each of them at a level higher than or equal to their specific Critical Compaction Concentration (CCC), respectively, the total concentration of said Performance Markers being higher than 1% by weight of the compacted perfume composition; at least one Performance Vehicle A2, the total concentration of said Performance Vehicle being higher than 10% by weight of the compacted perfume composition; and at least one Performing Diluent B1, the total concentration of said Performing Diluents being higher than 5% by weight of the compacted perfume composition.

13 Claims, No Drawings

PERFUME COMPOSITIONS

This is an application filed under 35 USC 371 based on PCT/EP2016/066634, which in turn is based on and claims priority to GB 1512585.9 filed 17 Jul. 2015. The present application claims the full priority benefit of these prior applications and herein incorporates by reference the full disclosures of these prior applications. This invention relates to compacted perfume compositions. The invention further relates to methods of making said perfume compositions, as well as their use in fine fragrances and consumer products, such as personal care, laundry care and household care products. The invention also relates to fine fragrances and consumer products containing said perfume compositions.

The nature of liquid detergent products has been evolving in two opposite directions in recent years. On the one hand, in dilute systems, there has been a tendency to reduce the level and/or quality of surface active ingredients in response to the demand for low-cost products. Whereas, on the other hand, highly concentrated bases have emerged that are characterized by low levels of water and high levels of surfactants, which surfactants form structured phases, sometimes called mesophases.

These trends pose problems for perfumers: For example, in the case of the dilute systems, the lower levels and/or poor quality of surfactant means that they have less solubilizing power for perfume ingredients, and at high perfume loading these systems can become cloudy or turbid, or their thermal stability window is narrowed. In highly concentrated surfactant systems the situation is no less complicated, as perfume ingredients in high concentrations can cause undesirable interactions with structured surfactant phases, resulting in gelation or phase separation issues. High perfume levels are also known to cause colouration issues as a result of Schiff base formation, oxidation, or metal complexation.

The effects of high perfume concentration can also create problems in powdered or granulated detergent products, particularly those intended to be used at low dosage. High perfume levels may be detrimental to the solubility or the dispersibility of these products in water, due to hydrophobic interactions. On the other hand, particulate products containing relatively high levels of perfume may become sticky, tacky or greasy, which can be detrimental to their handling properties. Sticky or tacky particles are also prone to agglomeration, which in turn affects the pourability and flowability of the particulate product. Greasy products are aesthetically not acceptable and may confer greasiness to surfaces with which they come into contact.

Merely taking a perfume composition designed for use at a particular concentration and lowering the amount used in these products often does not result in a desirable outcome. Lowering the concentration of standard perfume formulations in consumer products may lead to perfume performance issues. For example, the level of perfume in a consumer product may not be strong enough to cover the intrinsic smell of that product, leading to its rejection by consumers. Or the initial impact and bloom of the perfume in use may not be sufficient to convince the consumer of the quality and power of the product during application. There may also be insufficient perfume remaining on surfaces or substrates to guarantee sufficient odour substantivity or tenacity over time, for example after drying.

This can be particularly problematic with detergent products in compacted form. Compacted products are characterized by enhanced functional efficiency in terms of washing or conditioning power and require significantly lower dosage in end consumer applications. Typically, the dosage of a compacted product may be less than two to five times the unit dose of conventional products, so that the total amount of perfume delivered at all stages of the application is much lower than that delivered by conventional products, and deficiency in terms of potential odour impact may become a serious issue. This is observed, for example, in the case of compacted laundry detergents. Such compacted detergents show a better environmental sustainability profile compared to un-compacted products, but the relatively small size of the unit dose results in significantly lower perfume delivery throughout the wash cycle, thereby imparting less odour to a treated substrate, compared to conventional products. As such, compacted products may receive lower acceptance by those consumers who are driven by perfume quality or for whom the perfume intensity is a key product performance indicator.

Hence, there is a need for perfume compositions, particularly suitable for use in compacted products, which impart odour benefit throughout an application that is comparable with perfume benefits obtained using conventional perfumes delivered through non-compacted products. In particular, there is a need for compacted perfume compositions that deliver similar performance profiles in terms of intensity on neat product (impact), bloom (radiance), substantivity, room filling (volume) and trail (sillage), compared to conventional perfume compositions delivered at conventional levels.

Applicant attempted to address this problem using a "top down" approach to perfume design. In a top-down creation process, one starts from an conventional perfume formula that would be typically employed in non-compacted detergent products, before reducing the volume of its component perfume ingredients whilst trying to maintain the desired overall performance profile and hedonic pleasantness. In such an approach, the formulator first removes solvents and low odour perfumery ingredients or fillers, or diluents from the conventional perfume formula.

Applicant found, however, in laundry application, that although this practice can retain the impact of a perfume in the early stages of an application, such as for example in its container or on when deposited on wet substrates, it generally does not impart enough odour strength at later stages of an application, such as for example during dry-down or on dry substrates. In fact, removing solvents and low odour ingredients results merely in applying a concentration factor that never exceeds 10 (if solvents and low odour materials account for 90% of the perfume formula) and more generally does not exceed 2 to 3 (if solvents and low odour ingredients account for 50% to 33% of the perfume formula). Such concentration factors are by far too low to provide the desired perfume performance profile at all stages of application.

Furthermore, increasing the level of high impact odorants in a conventional perfume formula, after the solvents and low odour ingredients have been removed, also does not provide a desirable outcome. The applicant found that such manipulations neither result in desired performance profiles, nor lead to balanced perfumes. Rather, perfumes constructed in this way are characterized by harsh, unpleasant odours when they are smelled in container through to dry substrates. The harmony of the initial perfume formula is often disrupted and the hedonic profile may be far away from that of the initial formula.

In fact, applicant found that starting with what is essentially a finished perfume formula suitable for use in conventional non-compacted detergent products, and compacting it in the manner described above—the so-called "top-down" approach—is difficult, if not impossible, to implement. This is particularly the case of perfume formulae having a floral character. The reason is that high impact ingredients remaining in a formula after removing the solvents and low odour ingredients and which have a citrus, green or floral character are either scarce and difficult to find, or unpleasant, or are too typical of a certain odour direction. For example, compacting a floral accord using the top-down creation approach, often produces a violet or a white flower note, while a lily of the valley or a rose or a freesia note will remain out of reach using this technique.

In its quest for an effective approach to perfume compaction, and after considerable research effort, the applicant found that applying a "bottom-up" creation process, the task of providing both performant and pleasant-smelling perfume formulae, particularly useful in compacted detergent products, was rendered simpler and more reproducible across all manner of odour directions, but particularly for perfume formulae having citrus, green or floral character.

This so-called "bottom-up" creation process is articulated in the form of a series of perfume selection rules, following which a compacted perfume composition may be constructed, whereby a sub-composition A of the compacted perfume composition capturing desirable performance features, such as intensity in neat product, bloom, substantivity, room filling and trail, is constructed and is admixed with a sub-composition B, designed for hedonic pleasantness.

Accordingly, the invention provides in a first aspect a compacted perfume composition comprising a sub-composition A and a sub-composition B, wherein the sub-composition A comprises at least three, preferably at least four, most preferably at least five Performance Marker ingredients A1 and at least one, preferably at least three, most preferably at least five Performance Vehicle ingredients A2; and the sub-composition B comprises at least one Performing Diluent B1 and optionally one or more other fragrance ingredients B2.

The advantages of creating perfume compositions using the perfume selection criteria disclosed herein are manifold.

In particular, compacted perfume compositions provide similar odour performance as conventionally prepared perfume compositions, but they deliver their performance at a significantly lower dosage.

Advantages attendant to this lower dosing include lower formulation costs; ease of compliance with more stringent regulatory requirements limiting the usage levels of certain perfumery ingredients; environmental impact, in terms of reduced resource consumption and ecological imprint; as well as permitting the use of the newly emerging more powerful perfume ingredients in the perfumers' palette, which will enable new, exciting and more polarizing perfume benefits to be built into perfume compositions.

From the perspective of technical advantages, the compacted perfume compositions have minimal impact on the physical properties of consumer product bases, and particularly compacted consumer product bases, such as aspect, transparency, stability, viscosity, solubility and the like, compared to conventionally prepared perfume compositions dosed at conventional levels. This can be particularly useful given the fast moving consumer goods industry trend towards using bio-sourced solubilizing agents and solvents, which generally exhibit lower solubilizing power than their petrochemical analogues. Such formulations are less tolerant to high levels of perfume oils in terms of rheological and thermal stability.

The Performance Markers A1 are further characterised by a Critical Compaction Concentration (CCC in % by weight, based on the total weight of compacted perfume composition) which is ingredient specific. The CCC values have been determined empirically, based on perfumer knowledge and expertise, and constitute an embodiment of the present invention.

Therefore, in a particular embodiment of the present invention there is provided a compacted perfume composition as hereinabove described, wherein
A) at least three, preferably at least four, most preferably at least five Performance Markers A1 are present, each of them at a level higher than or equal to their Critical Compaction Concentration, respectively; and
B) the total concentration of the at least three, preferably at least four, most preferably at least five Performance Markers is higher than 1%, preferably higher than 2% and most preferably higher than 3% by weight of the compacted perfume composition.

The at least three, preferably at least four, most preferably at least five Performance Markers A1 can be selected from the group consisting of Acetal R ((2-(1-propoxyethoxy)ethyl)benzene, 0.25%); Acetophenone (acetophenone, 0.6%); Acetyl pyrazine (1-(pyrazin-2-yl)ethanone, 0.1%); Adoxal (2,6,10-trimethylundec-9-enal, 0.25%); Aldehyde C 11 MOA (2-methyldecanal, 0.5%); Aldehyde C 11 undecylenic (undec-10-enal, 0.7%); Aldehyde C 6 hexylic food grade (hexanal, 0.55%); Aldehyde C 7 heptylic (heptanal, 0.15%); Aldehyde C 9 isononylic (3,5,5-trimethylhexanal, 0.45%); Aldehyde iso C 11 ((E)-undec-9-enal, 0.75%); Amberketal® (3,8,8,11a-tetramethyldodecahydro-1H-3,5a-epoxynaphtho[2,1-c]oxepine, 0.05%); Ambermax® (1,3,4,5,6,7-hexahydro-.beta., 1,1,5,5-pentamethyl-2H-2,4a-methanonaphthalene-8-ethanol, 0.15%); Ambrinol (2,5,5-trimethyl-1,2,3,4,4a,5,6,7-octahydronaphthalen-2-ol, 0.1%); Ambrocenide® ((4aR,5R,7aS,9R)-Octahydro-2,2,5,8,8,9a-hexamethyl-4h-4a,9-methanoazuleno[5,6-d]-1,3-dioxole, 0.05%); Amyl vinyl carbinol (oct-1-en-3-ol, 0.2%); Azurone® (7-isopentyl-2H-benzo[b][1,4]dioxepin-3(4H)-one 0.005%); Bigaryl® (8-(sec-butyl)-5,6,7,8-tetrahydroquinoline, 0.01%); Buccoxime ((1R,5S,E)-1,5-dimethylbicyclo[3.2.1]octan-8-one oxime, 0.03%); Butyl quinoline secondary (6-(sec-butyl)quinoline, 0.1%); Calone® 1951 (7-methyl-2H-benzo[b][1,4]dioxepin-3(4H)-one, 0.2%); Caramel Lactone (3-hydroxy-4,5-dimethylfuran-2(5H)-one, 0.000075%); Carvacrol (5-isopropyl-2-methylphenol, 0.4%); Cassyrane™ (5-tert-butyl-2-methyl-5-propyl-2H-furan, 0.10%); Cetone V ((E)-1-(2,6,6-trimethylcyclohex-2-en-1-yl)hepta-1,6-dien-3-one, 0.5%); Citronellyl oxyacetaldehyde (2-((3,7-dimethyloct-6-en-1-yl)oxy)acetaldehyde, 0.2%); Corps Cassis (2-(2-mercaptopropan-2-yl)-5-methylcyclohexanone, 0.02%); Corps Pamplemousse ((4S)-4,7,7-trimethyl-6-thiabicyclo[3.2.1]octane, 0.3%); Corps Racine (2-(3-phenylpropyl)pyridine, 0.015%); Corylone dried (2-hydroxy-3-methylcyclopent-2-enone, 0.3%); Cresyl caprylate para (p-tolyl octanoate, 0.15%); Cresyl methyl ether para (1-methoxy-4-methylbenzene, 0.5%); Cumin nitrile (4-isopropylbenzonitrile, 0.05%); Cuminic aldehyde (4-isopropylbenzaldehyde, 0.2%); Damascenone ((E)-1-(2,6,6-trimethylcyclohexa-1,3-dien-1-yl)but-2-en-1-one, 0.1%); Damascone delta ((E)-1-(2,6,6-trimethylcyclohex-3-en-1-yl)but-2-en-1-one, 0.3%); Decanonitrile (decanenitrile, 0.3%); Decenal-2-trans ((E)-dec-2-enal, 0.01%); Decenal-4-trans ((E)-dec-4-enal, 0.1%); Decenal-9 (9-decenal, 0.05%); Dione (2-(2-(3,3,5-trimethylcyclohexyl)acetyl)cyclopentanone, 0.1%); Dodecenal ((E)-dodec-2-enal, 0.1%); Dupical ((E)-4-((3 aS,7aS)-hexahydro-1H-4,7-methanoinden-5(6H)-ylidene)butanal, 0.15%); Ethyl-3 dimethyl-2(5 or 6) pyrazine (Ethyl-3 dimethyl-2(5 or 6) pyrazine, 0.03%); Ethyl laitone (8-ethyl-1-oxaspiro[4.5]decan-2-one, 0.03%);

Evernyl (methyl 2,4-dihydroxy-3,6-dimethylbenzoate, 0.65%); Floridile® ((E)-undec-9-enenitrile, 0.15%); Folione (methyl oct-2-ynoate, 0.15%); Galbanone pure (1-(3,3-dimethylcyclohex-1-en-1-yl)pent-4-en-1-one, 0.2%); Guaiacol (2-methoxyphenol, 0.05%); Trans-2-hexenal (E-hex-2-enal, 0.15%); Homofuronol (2-ethyl-4-hydroxy-5-methylfuran-3 (2H)-one, 0.1%); Hydratropic aldehyde (2-phenylpropanal, 0.25%); Isobutyl methoxy pyrazine 1% EC (2-isobutyl-3-methoxypyrazine, 0.000005%); Isobutyl quinoline-2 (2-isobutylquinoline, 0.1%); Isoeugenol ((E)-2-methoxy-4-(prop-1-en-1-yl)phenol, 0.7%); Isopropyl quinoline (6-isopropylquinoline, 0.25%); Karanal (5-(sec-butyl)-2-(2,4-dimethylcyclohex-3-en-1-yl)-5-methyl-1,3-dioxane, 0.55%); Labienoxime ((3E,6E)-2,4,4,7-tetramethylnona-6,8-dien-3-one oxime, 0.05%); Maceal (bicyclo[2.2.2]oct-5-ene-2-carboxaldehyde, 0.1%); Methoxy methyl pyrazine (2-methoxy-3-methylpyrazine, 0.2%); Methyl corylone (2-hydroxy-3,4-dimethyl-2-cyclopenten-1-one, 0.4%); Methyl geosmin (4,4,8a-trimethyldecahydronaphthalen-4a-ol, 0.025%); Methyl isopropyl thiazole (2-ethyl-4-methyl-1,3-thiazole, 0.07%); Methyl Laitone (8-methyl-1-oxaspiro[4.5]decan-2-one, 0.15%); Methyl octyne carbonate (methyl non-2-ynoate, 0.1%); Neocaspirene extra (10-isopropyl-2,7-dimethyl-1-oxaspiro[4.5]deca-3,6-diene, 0.3%); Neofolione ((E)-methyl non-2-enoate, 0.45%); Nerolione (1-(3-methylbenzofuran-2-yl)ethanone, 0.15%); Nonadienal ((2E, 6Z)-nona-2,6-dienal, 0.02%); Cis-6-nonenal ((Z)-non-6-enal, 0.045%); Oxane (2-methyl-4-propyl-1,3-oxathiane, 0.1%); Grapefruit mercaptan (2-(4-methylcyclohex-3-en-1-yl)propane-2-thiol, 0.0000065%); Paramenthone (5-methyl-2(2-methylethyl)-cyclohexanone, 0.01%); Pharaone® (2-cyclohexylhepta-1,6-dien-3-one, 0.1%); Phenyl acetaldehyde (2-phenyl-ethanal, 0.2%); Pomarose ((2E,5E)-5,6,7-trimethylocta-2,5-dien-4-one 0.05%); Pyralone (6-(sec-butyl)quinoline, 0.1%); Rosalva (dec-9-en-1-ol, 0.4%); Rose Oxide (4-methyl-2-(2-methylprop-1-en-1-yl)tetrahydro-2H-pyran, 0.4%); Rosyrane super (4-methylene-2-phenyltetrahydro-2H-pyran, 0.10%); Safraleine (2,3,3-trimethyl-2,3-dihydro-1H-inden-1-one, 0.1%); Safranal (2,6,6-trimethylcyclohexa-1,3-dienecarbaldehyde, 0.05%); Shisolia™ (4-vinylcyclohex-1-enecarbaldehyde, 0.15%); Spirogalbanone (1-spiro[4.5]dec-7-en-7-yl-4-penten-1-one, 0.15%); Syringa aldehyde (2-(p-tolyl)acetaldehyde, 0.1%); Thiogeraniol ((E)-3,7-dimethylocta-2,6-diene-1-thiol, 0.05%); Tolyl aldehyde para extra (4-methylbenzaldehyde, 1%); Toscanol (1-(cyclopropylmethyl)-4-methoxybenzene, 0.10%); Trans-2-hexenal (E-hex-2-enal, 0.15%); Tridecenonitrile ((E)-tridec-2-enenitrile, 0.1%); Trifernal (3-phenylbutanal, 0.5%); Ultravanil (2-ethoxy-4-methylphenol, 0.15%); Undecatriene ((3E,5Z)-undeca-1,3,5-triene, 0.05%); Trans 2 undecenal ((E)-undec-2-enal, 0.1%); Verdoracine ((E)-4-isopropyl-1-methyl-2-(prop-1-en-1-yl)benzene, 0.25%); Violet nitrile ((2E,6Z)-nona-2,6-dienenitrile, 0.01%); Zinarine® (2-(2,4-dimethylcyclohexyl)pyridine, 0.05%).

The Performance Markers A1 listed above include parenthetical reference to their IUPAC nomenclature and respective CCC values (% by weight, based on the total weight of compacted perfume composition).

In an embodiment of the invention, a sub-composition A is prepared when at least three, preferably at least four, most preferably at least five Performance Markers A1 are selected and employed at a level equal to or superior to their specific Critical Compaction Concentration.

The at least one, preferably at least three, most preferably at least five Performance Vehicles A2 can be selected from the group consisting of Aldehyde C 12 Lauric (dodecanal); Aldehyde C 12 MNA (2-methylundecanal); Ambrettolide ((Z)-oxacycloheptadec-10-en-2-one); Ambrofix™ (3a,6,6,9a-tetramethyldodecahydronaphtho[2,1-b]furan); Ambroxan (3a,6,6,9a-tetramethyldodecahydronaphtho[2,1-b]furan); Anethole synthetic ((E)-1-methoxy-4-(prop-1-en-1-yl)benzene); Aubepine para cresol (4-methoxybenzaldehyde); Butyl butyrate (butyl butanoate); Calypsone® (6-methoxy-2,6-dimethyloctanal); Citral ((E)-3,7-dimethylocta-2,6-dienal); Citral dimethyl acetal ((E)-1,1-dimethoxy-3,7-dimethylocta-2,6-diene); Citral diethyl acetal ((E)-1,1-diethoxy-3,7-dimethylocta-2,6-diene); Citrathal® R ((Z)-1,1-diethoxy-3,7-dimethylocta-2,6-diene); Citronellal (3,7-dimethyloct-6-enal); Citronellyl nitrile (3,7-dimethyloct-6-enenitrile); Claritone (2,4,4,7-tetramethyloct-6-en-3-one); Cosmone® ((Z)-3-methylcyclotetradec-5-enone); Coumarin (2H-chromen-2-one); Cresol para (p-cresol); Cyclemone A (8,8-dimethyl-1,2,3,4,5,6,7,8-octahydronaphthalene-2-carbaldehyde); Isocyclocitral (2,4,6-trimethylcyclohex-3-enecarbaldehyde); Cyclogalbanate (allyl 2-(cyclohexyloxy)acetate); Damascone alpha ((E)-1-(2,6,6-trimethylcyclohex-2-en-1-yl)but-2-en-1-one); Decatone (6-isopropyloctahydronaphthalen-2(1H)-one); Dihydro jasmone (3-methyl-2-pentylcyclopent-2-enone); Dihydro anethole (1-methoxy-4-propylbenzene); Dihydro eugenol (2-methoxy-4-propylphenol); Dimethyl octenone (4,7-dimethyloct-6-en-3-one); Ebanol® ((E)-3-methyl-5-(2,2,3-trimethylcyclopent-3-en-1-yl)pent-4-en-2-ol); Elintaal (3-(1-ethoxyethoxy)-3,7-dimethylocta-1,6-diene); Ethyl butyrate (ethyl butyrate); Ethyl maltol (2-ethyl-3-hydroxy-4H-pyran-4-one); Ethyl safranate (ethyl 2,6,6-trimethylcyclohexa-1,3-diene-1-carboxylate); Ethyl vanillin (3-ethoxy-4-hydroxybenzaldehyde); Ethyl-2-methyl butyrate (ethyl 2-methylbutanoate); Ethyl salicylate (ethyl 2-hydroxybenzoate); Florhydral® (3-(3-isopropylphenyl)butanal); Florocyclene ((3aR,6S,7aS)-3a,4,5,6,7,7a-hexahydro-1H-4,7-methanoinden-6-yl propionate); Frescile (3-methyldodecanenitrile); Gardamide (N,2-dimethyl-N-phenylbutanamide); Gardocyclene ((3aR,6S,7aS)-3a,4,5,6,7,7a-hexahydro-1H-4,7-methanoinden-6-yl isobutyrate); Geranium essence; Geranodyle (2-(2-hydroxypropan-2-yl)-5-methylcyclohexanol); Herbavert™ (3-ethoxy-1,1,5-trimethylcyclohexane); Iso jasmone (2-hexylcyclopent-2-enone); Isoraldeine® 70 ((E)-3-methyl-4-(2,6,6-trimethylcyclohex-2-en-1-yl)but-3-en-2-one); Jasmacyclene ((3aR,6S,7aS)-3a,4,5,6,7,7a-hexahydro-1H-4,7-methanoinden-6-yl acetate); Jasmatone (2-hexylcyclopentanone); Javanol ((1-methyl-2-((1,2,2-trimethylbicyclo[3.1.0]hexan-3-yl)methyl)cyclopropyl)methanol); Leaf acetal ((Z)-1-(1-ethoxyethoxy)hex-3-ene); Lemonile™ ((2E,6Z)-3,7-dimethylnona-2,6-dienenitrile); Liffarome ((Z)-hex-3-en-1-yl methyl carbonate); Ligantraal ((E)-methyl 2-(((2,4-dimethylcyclohex-3-en-1-yl)methylene)amino)benzoate); Linalool oxide (2-(5-methyl-5-vinyltetrahydrofuran-2-yl)propan-2-ol); Manzanate (ethyl 2-methylpentanoate); Mefranal (3-methyl-5-phenylpentanal); Melonal™ (2,6-dimethylhept-5-enal); Methyl acetophenone (1-(p-tolyl)ethanone); Methyl isoeugenol ((E)-1,2-dimethoxy-4-(prop-1-en-1-yl) benzene); Methyl salicylate (methyl 2-hydroxybenzoate); Muscenone™ ((Z)-3-methylcyclopentadec-5-enone); Nectaryl (2-(2-(4-methylcyclohex-3-en-1-yl)propyl)cyclopentanone); Paradisamide® (2-ethyl-N-methyl-N-(m-tolyl) butanamide); Patchouli essence; Peach Pure (5-heptyldihydrofuran-2(3H)-one); Peonile® (2-cyclohexylidene-2-phenylacetonitrile); Petalia® (2-cyclohexylidene-2-(o-tolyl) acetonitrile); Pinoacetaldehyde (3-(6,6-dimethylbicyclo [3.1.1]hept-2-en-2-yl)propanal); Pivacyclene ((3aR,6S, 7aS)-3a,4,5,6,7,7a-hexahydro-1H-4,7-methanoinden-6-yl pivalate); Polysantol® ((E)-3,3-dimethyl-5-(2,2,3-trimethyl-3-cyclopenten-1-yl)-4-penten-2-ol); Prunolide (5-pentyldihydrofuran-2(3H)-one); Quintone® (2-pentylcyclopentanone); Radjanol ((E)-2-ethyl-4-(2,2,3-trimethylcyclopent-3-en-1-yl)but-2-en-1-ol); Raspberry ketone (4-(4-hydroxyphenyl)butan-2-one); Rhubafuran (2,4-dimethyl-4-phenyltetrahydrofuran); Rhubofix® ((2R,8aS)-3',6-dimethyl-3,4,4a,5,8,8a-hexahydro-1H-spiro[1,4-methanonaphthalene-2,2'-oxirane]); Rossitol™ (3-isobutyl-1-methylcyclohexanol); Seringone (methyl 2-((E)-((E)-2-benzylideneheptylidene)amino)benzoate); Silvanone® (cyclopentadecanone and hexadecanolide); Stemone® ((E)-5-methylheptan-3-one oxime); Sylkolide™ ((E)-2-((3,5-dimethylhex-3-en-2-yl)oxy)-2-methylpropyl cyclopropanecarboxylate); Timberol® (1-(2,2,6-trimethylcyclohexyl) hexan-3-ol); Tolyl aldehyde para (4-methylbenzaldehyde); Undecavertol ((E)-4-methyldec-3-en-5-ol); Vanillin (4-hydroxy-3-methoxybenzaldehyde); Vanitrope ((E)-2-ethoxy-5-(prop-1-en-1-yl)phenol); Velvione® ((Z)-cyclohexadec-5-enone); Vetikol acetate/Corps Rhubarbe (4-methyl-4-phenylpentan-2-yl acetate); Yara Yara (2-methoxynaphthalene); (4E)-9-hydroxy-5,9-dimethyl-4-decenal; 1-methyl-2-(5-methylhex-4-en-2-yl)cyclopropyl)-methanol; 3-(4-isobutyl-2-methylphenyl)propanal.

A sub-composition A according to the present invention contains at least one, preferably at least three, most preferably at least five Performance Vehicles A2.

In an embodiment of the invention, the total concentration of Performance Vehicles A2 in the compacted perfume composition is higher than 10% by weight, preferably higher than 15% by weight and still more preferably higher than 20% by weight of the compacted perfume composition.

The sub-composition B, especially designed for adding hedonic pleasantness to the compacted perfume composition, comprises at least one so-called Performing Diluent B1, selected from the group consisting of Agrumex (2-(tert-butyl)cyclohexyl acetate); Amyl salicylate (pentyl 2-hydroxybenzoate); Applelide (propanedioic acid 1-(1-(3,3-dimethylcyclohexyl)ethyl) 3-ethyl ester); Benzyl salicylate (benzyl 2-hydroxybenzoate); Camphor ((1S,4S)-1,7,7-trimethylbicyclo[2.2.1]heptan-2-one); Citronellol (3,7-dimethyloct-6-en-1-ol); Citrus essence; Cyclamen aldehyde (3-(4-isopropylphenyl)-2-methylpropanal); Cyclohexyl salicylate (cyclohexyl 2-hydroxybenzoate); Cyprisate® (methyl 1,4-dimethylcyclohexanecarboxylate); Dihydro ambrettolide (1-oxacycloheptadecan-2-one); Dihydrojasmone (3-methyl-2-pentylcyclopent-2-enone); Dihydro myrcenol (2,6-dimethyloct-7-en-2-ol); Dimetol® (2,6-dimethylheptan-2-ol); Dimyrcetol (2,6-dimethyloct-7-en-2-yl formate); Dipentene (1-methyl-4-(prop-1-en-2-yl)cyclohex-1-ene); Ethylene Brassylate (1,4-dioxacycloheptadecane-5,17-dione); Eucalyptol ((1s,4s)-1,3,3-trimethyl-2-oxabicyclo[2.2.2]octane); Fixolide® (1-(3,5,5,6,8,8-hexamethyl-5,6,7,8-tetrahydronaphthalen-2-yl)ethanone); Florosa™ (tetrahydro-4-methyl-2-(2-methylpropyl)-2H-pyran-4-ol); Freskomenthe® (2-(sec-butyl)cyclohexanone); Galaxolide® (4,6,6,7,8,8-hexamethyl-1,3,4,6,7,8-hexahydrocyclopenta[g]isochromene); Gardenol (1-phenylethyl acetate); Georgywood® (1-(1,2,8,8-tetramethyl-1,2,3,4,5,6,7,8-octahydronaphthalen-2-yl)ethanone); Geraniol ((E)-3,7-dimethylocta-2,6-dien-1-ol); Habanolide® ((E)-oxacyclohexadec-12-en-2-one); methyl 3-oxo-2-pentylcyclopentaneacetate (for example HedioneM); Helvetolide® (2-(1-(3,3-dimethylcyclohexyl)ethoxy)-2-methylpropyl propionate); Herbanate ((2S)-ethyl 3-isopropylbicyclo[2.2.1]hept-5-ene-2-carboxylate); Herboxane (2-butyl-4,4,6-trimethyl-1,3-dioxane); Hexyl salicylate (hexyl 2-hydroxybenzoate); Hydroxycitronellal (7-hydroxy-3,7-dimethyloctanal); Ionone beta ((E)-4-(2,6,6-trimethylcyclohex-1-en-1-yl)but-3-en-2-one); Iso E Super® (1-(2,3,8,8-tetramethyl-1,2,3,4,5,6,7,8-octahydronaphthalen-2-yl)ethanone); Karmaflor® ((4Z)-hept-4-en-2-yl 2-hydroxybenzoate); Lilial™ (3-(4-(tert-butyl)phenyl)-2-methylpropanal); Lime oxide; Linalool (3,7-dimethylocta-1,6-dien-3-ol); Mayol® ((4-isopropylcyclohexyl)methanol); Methyl pamplemousse (6,6-dimethoxy-2,5,5-trimethylhex-2-ene); Moxalone (1a,3,3,4,6,6-hexamethyl-1a,2,3,4,5,6,7,7a-octahydronaphtho[2,3-b]oxirene); Musk C14 (1,4-dioxacyclohexadecane-5,16-dione); Musk CPD (cyclopentadecanone); Musk R1 (1,7-dioxacycloheptadecan-8-one); Nirvanolide® ((E)-13-methyloxacyclopentadec-10-en-2-one); Okoumal® (2,4-dimethyl-2-(5,5,8,8-tetramethyl-5,6,7,8-tetrahydronaphthalen-2-yl)-1,3-dioxolane); Orange essence; Para-tert-butyl-cyclohexyl acetate (4-(tert-butyl)cyclohexyl acetate); Phenyl ethyl alcohol (2-phenylethanol); Romandolide® (acetic acid (1-oxopropoxy)-, 1-(3,3-dimethyl cyclohexyl)ethyl ester); Rosamusk (1-(3,3-dimethylcyclohexyl)ethyl acetate); Rhodinol; Serenolide (2-(1-(3,3-dimethylcyclohexyl)ethoxy)-2-methylpropyl cyclopropanecarboxylate); Silvial® (3-(4-isobutylphenyl)-2-methylpropanal); Tangerinol ((E)-6,10-dimethylundeca-5,9-dien-2-yl acetate); Tetrahydro linalool (3,7-dimethyloctan-3-ol); Thibetolide™ (oxacyclohexadecan-2-one).

In an embodiment of the invention, the sub-composition B contains at least one, preferably at least three, most preferably at least five Performing Diluents B1.

In a particular embodiment of the present invention, the total concentration of Performing Diluents B1 in a compacted perfume composition is higher than 5% by weight, preferably higher than 15% by weight and still more preferably higher than 25% by weight of the compacted perfume composition.

Sub-composition B optionally contains any other fragrance ingredient B2, such as those described in S. Arctander "Perfume and Flavor Chemicals: Volume 1, Allured Publishing Corporation 1969, or any later editions thereof, as well as the IFRA (International Fragrance Research Association) database, and RIFM (Research Institute of Fragrance Materials) database, each of which and hereby incorporated by reference in their entirety, and wherein the other fragrance ingredient B2 is belonging to none of the groups A1, A2 and B1 identified above, and wherein the other fragrance ingredients are not low odour ingredients as defined below.

The compacted perfume composition according to the present invention is furthermore substantially free of any low odour ingredients, wherein the term "substantially free" is meant that the level of low odour ingredients is lower than 3%, preferably lower than 2% by weight and still more preferably lower than 1% by weight of the compacted perfume composition.

The term "low odour ingredients" means those ingredients having an Odour Value lower than 100, wherein the Odour Value of a perfume ingredient is defined as the ratio of the Standard Equilibrium Headspace Concentration, expressed in microgram/l, to the Odour Detection Threshold, also expressed in microgram/l. "Odour Detection Threshold" (ODTi) refers to the average concentration above which an odorant (i) can be perceived by a panelist and can be measured using an olfactometer.

"Standard Equilibrium Headspace Concentration" refers to the concentration of an ingredient in equilibrium with its condensed form (that is, its solid or liquid form) at a temperature of 25° C. and under a pressure of 1 atmosphere.

It can be measured by using any of the known quantitative headspace analysis techniques, see for example Mueller and Lamparsky in Perfumes: Art, Science and Technology, Chapter 6 "The Measurement of Odors" at pages 176-179 (Elsevier 1991).

The low odour ingredients according to the present invention include solvents.

Typical solvents that are "low odour ingredients" according to the invention, and which are particularly undesired in compacted perfume compositions according to the present invention include Ethanol, Isopropanol, Propylene glycol, Dipropylene glycol, Glycol ethers available commercially under the Trade Mark Dowanol®, such as Dowanol® DPMA (dipropylene glycol methyl ether acetate), Dowanol® DPM (dipropylene glycol methyl ether), Dowanol TPM (tripropylene glycol methyl ether), Dowanol DPNB (propylene glycol n-butyl ether, Dowanol DPNP (propylene glycol n-propyl ether), and other suitable Dow Chemical as Dow P-series glycol ethers, dibasic ester DBE (blend composed of Diisobutyl glutarate, Diisobutyl succinate, and Diisobutyl adipate, commercially available from Solvay, or blend composed of Diisobutyl glutarate, and Diisobutyl adipate, commercially available from Invista), methyl methoxy butanol(+/−)-2,2-dimethyl-4-hydroxymethyl-1,3-dioxolane, commercially available from Solvay under the name Augeo Clean Multi®, dimethyl isosorbide, Isopropyl myristate, Triethyl citrate, Acetyl tributyl citrate, Diethyl phthalate, methyl myristate, alkyl esters, such as methyl linoleate, methyl palmitate, ethyl laurate, ethyl linoleate, ethyl oleate, ethyl octanoate, dibenzyl ether and diethyl phtalate, and hydrocarbons, such as Isopar® H, Isopar® dibenzyl ether dibenzyl ether M and Isopar® L, commercially available from Exxon and mixture thereof.

In an embodiment of the invention, the total concentration of low odour ingredients in a compacted perfume composition is lower than 3% by weight, preferably lower than 2% by weight and still more preferably lower than 1% by weight based on the weight of the compacted perfume composition.

In a particular embodiment of the present invention there is provided a compacted perfume composition comprising:
a) at least three, preferably at least four, most preferably at least five Performance Markers A1, each of them at a level higher than or equal to their specific Critical Compaction Concentration (CCC), respectively, the total concentration of said Performance Markers being higher than 1%, preferably higher than 2% and most preferably higher than 3% by weight of the compacted perfume composition;
b) at least one, preferably at least three, most preferably at least five Performance Vehicle A2, the total concentration of said Performance Vehicle being higher than 10% by weight, preferably higher than 20% by weight and still more preferably higher than 25% by weight of the compacted perfume composition; and
c) at least one, preferably at least three, most preferably at least five Performing Diluents B1, the total concentration of said Performing Diluents being higher than 5% by weight, preferably higher than 15% by weight and still more preferably higher than 25% of the compacted perfume composition.

In a more particular embodiment, the compacted perfume composition further optionally comprises one or more perfumery ingredient B2 belonging to none of the groups A1, A2 and B1, and not being a low odour ingredient.

In a more particular embodiment, the compacted perfume composition comprises less than 3% by weight, preferably less than 2% by weight and still more preferably less than 1% by weight of low odour ingredients having an Odour Value of less than 100. Compacted perfume compositions containing such amounts of low odour ingredients can be packed, stored and transported efficiently.

Having regard to the teaching of the present invention, it will be obvious to the skilled person that the selection of ingredients A1, A2, B1 and optionally B2 defined herein above, will be sympathetic to hedonic requirements of a particular compacted perfume compositions, requiring a desired odour direction or theme, or by the overall requirement that the composition must be pleasant to the consumer. Obviously, provided the perfumery rules are respected, the specific composition of sub-compositions A and B in a floral compacted perfume composition may certainly be different from that of fruity, woody or oriental compacted perfume compositions.

Hence, in a particular embodiment, the ingredients A1, A2, B1 and optionally B2 may be selected in such a way that sub-compositions A and B are particularly suitable for the "bottom-up" creation of floral accords.

Preferred Performance Markers A1, particularly suitable for the bottom-up creation of floral accords, include Acetal R ((2-(1-propoxyethoxy)ethyl)benzene, 0.25%); Acetophenone (acetophenone, 0.6%); Adoxal (2,6,10-trimethylundec-9-enal, 0.25%); Aldehyde C 11 MOA (2-methyldecanal, 0.5%); Aldehyde C 11 undecylenic (undec-10-enal, 0.7%); Aldehyde C 6 hexylic food grade (hexanal, 0.55%); Aldehyde C 7 heptylic (heptanal, 0.15%); Aldehyde C 9 isononylic (3,5,5-trimethylhexanal, 0.45%); Aldehyde iso C 11 ((E)-undec-9-enal, 0.75%); Bigaryl® (8-(sec-butyl)-5,6,7,8-tetrahydroquinoline, 0.01%); Citronellyl oxyacetaldehyde (2-((3,7-dimethyloct-6-en-1-yl)oxy)acetaldehyde, 0.2%); Damascenone ((E)-1-(2,6,6-trimethylcyclohexa-1,3-dien-1-yl)but-2-en-1-one, 0.1%); Damascone delta ((E)-1-(2,6,6-trimethylcyclohex-3-en-1-yl)but-2-en-1-one, 0.3%); Decenal-2-trans ((E)-dec-2-enal, 0.01%); Decenal-4-trans ((E)-dec-4-enal, 0.1%); Decenal-9 (9-decenal, 0.05%); Dupical ((E)-4-((3aS,7aS)-hexahydro-1H-4,7-methanoinden-5(6H)-ylidene)butanal, 0.15%); Floridile® ((E)-undec-9-enenitrile, 0.15%); Folione® (methyl oct-2-ynoate, 0.15%); Neofolione ((E)-methyl non-2-enoate, 0.45%); Nerolione (1-(3-methylbenzofuran-2-yl)ethanone, 0.15%); Nonadienal ((2E,6Z)-nona-2,6-dienal, 0.02%); Cis-6-nonenal ((Z)-non-6-enal, 0.045%); Phenyl acetaldehyde (2-phenyl-ethanal, 0.2%); Pomarose ((2E,5E)-5,6,7-trimethylocta-2,5-dien-4-one, 0.05%); Rosalva (dec-9-en-1-ol, 0.4%); Rose Oxide (4-methyl-2-(2-methylprop-1-en-1-yl)tetrahydro-2H-pyran, 0.4%); Rosyrane super (4-methylene-2-phenyltetrahydro-2H-pyran, 0.10%); Syringa aldehyde (2-(p-tolyl)acetaldehyde, 0.1%); Tolyl aldehyde para extra (4-methylbenzaldehyde, 1%); Trifernal (3-phenylbutanal, 0.5%); Verdoracine ((E)-4-isopropyl-1-methyl-2-(prop-1-en-1-yl)benzene, 0.25%); Violet nitrile ((2E,6Z)-nona-2,6-dienenitrile, 0.01%); and Zinarine® (2-(2,4-dimethylcyclohexyl)pyridine, 0.05%).

Preferred Performance Vehicles A2, particularly suitable for the bottom-up creation of floral accords, include Aubepine para cresol (4-methoxybenzaldehyde); Butyl butyrate (butyl butanoate); Dihydro jasmone (3-methyl-2-pentylcyclopent-2-enone); Florhydral® (3-(3-isopropylphenyl)butanal); Florocyclene ((3aR,6S,7aS)-3a,4,5,6,7,7a-hexahydro-1H-4,7-methanoinden-6-yl propionate); Geranium essence; Geranodyle (2-(2-hydroxypropan-2-yl)-5-methylcyclohexanol); Isoraldeine® 70 ((E)-3-methyl-4-(2,6,6-trimethylcyclohex-2-en-1-yl)but-3-en-2-one); Jasmacyclene ((3aR,6S,7aS)-3a,4,5,6,7,7a-hexahydro-1H-4,7-methanoinden-6-yl acetate); Mefranal (3-methyl-5- phenylpentanal); Methyl acetophenone (1-(p-tolyl) ethanone); Nectaryl (2-(2-(4-methylcyclohex-3-en-1-yl)propyl)-cyclopentanone); Patchouli essence; Peonile (2-cyclohexylidene-2-phenylacetonitrile); Petalia® (2-cyclohexylidene-2-(o-tolyl)acetonitrile); Quintone® (2-pentylcyclopentanone); Rossitol™ (3-isobutyl-1-methylcyclohexanol); Seringone (methyl 2-((E)-((E)-2-benzylideneheptylidene)amino)benzoate); Velvione® ((Z)-cyclohexadec-5-enone); Yara Yara (2-methoxynaphthalene); (4E)-9-hydroxy-5,9-dimethyl-4-decenal; 1-methyl-2-(5-methylhex-4-en-2-yl)cyclopropyl)methanol; 3-(4-isobutyl-2-methylphenyl)propanal.

Preferred Performing Diluents B1, particularly suitable for the bottom-up creation of floral accords, include: Agrumex (2-(tert-butyl)cyclohexyl acetate); Amyl salicylate (pentyl 2-hydroxybenzoate); Benzyl salicylate (benzyl 2-hydroxybenzoate); Cyclamen aldehyde (3-(4-isopropylphenyl)-2-methylpropanal); Citronellol (3,7-dimethyloct-6-en-1-ol); Cyclohexyl salicylate (cyclohexyl 2-hydroxybenzoate); Dihydrojasmone (3-methyl-2-pentylcyclopent-2-enone); Dihydro myrcenol (2,6-dimethyloct-7-en-2-ol); Fixolide® (1-(3,5,5,6,8,8-hexamethyl-5,6,7,8-tetrahydronaphthalen-2-yl)ethanone); Florosa™ (tetrahydro-4-methyl-2-(2-methylpropyl)-2H-pyran-4-ol); Freskomenthe® (2-(sec-butyl)cyclohexanone); Galaxolide® (4,6,6,7,8,8-hexamethyl-1,3,4,6,7,8-hexahydrocyclopenta[g]isochromene); Gardenol (1-phenylethyl acetate); Geraniol ((E)-3,7-dimethylocta-2,6-dien-1-ol); Habanolide® ((E)-oxacyclohexadec-12-en-2-one); Helvetolide® (2-(1-(3,3-dimethylcyclohexyl)ethoxy)-2-methylpropyl propionate); Hexyl salicylate (hexyl 2-hydroxybenzoate); Hydroxycitronellal (7-hydroxy-3,7-dimethyloctanal); Ionone beta ((E)-4-(2,6,6-trimethylcyclohex-1-en-1-yl)but-3-en-2-one); Karmaflor® ((4Z)-hept-4-en-2-yl 2-hydroxybenzoate); Lilial™ (3-(4-(tert-butyl)phenyl)-2-methylpropanal); Orange essence; Phenyl ethyl alcohol (2-phenylethanol); Rosamusk (1-(3,3-dimethylcyclohexyl) ethyl acetate); Rhodinol; Silvial® (3-(4-isobutylphenyl)-2-methylpropanal); and Tetrahydro linalool (3,7-dimethyloctan-3-ol).

The compacted perfume compositions according to the present invention are preferably used at lower dosage in consumer products than conventional, that is un-compacted, perfumes. Preferably, the compacted perfume compositions are used at 50% by weight or less of the dosage of conventional perfumes, for example less than 40% by weight, less than 30% by weight, less than 20% by weight or less than 10% by weight of the dosage of conventional perfume. For example, if the typical dosage of a conventional perfume in a given consumer product is from about 0.5 to about 1.5% by weight, then the dosage of a compacted perfume composition will be from about 0.01 to 0.75% by weight, more particularly from about 0.05 to 0.5% by weight and still more particularly from about 0.1 to 0.25% by weight of the consumer product.

Typical consumer products concerned by the present invention include laundry care detergents, laundry care conditioners, fabric refreshers, personal care cleansing compositions, such as shampoos, bath and shower gels, liquid soaps, soap bars and the like, personal care conditioning composition, such as hair care conditioners, bath and shower lotions, deodorant compositions, antiperspirant compositions, home care compositions, such as hard surface cleaners, heavy duty detergents and the like, air care compositions, such as passive and active gel and wax air fresheners, plugins, candles and the like, as well as hydro-alcoholic and water-based fine fragrance compositions, body mist and the like.

In many cases, and especially in the laundry care, personal care and home care categories, the consumer products concerned by the present invention contain surfactants.

In a particular embodiment of the present invention there is provided a consumer product comprising a compacted perfume composition and at least one surfactant, selected from anionic, cationic, amphoteric or non-ionic surfactants. Typical anionic surfactants include but are not limited to sodium lauryl sulfate, sodium laureth sulfate, sodium trideceth sulfate, ammonium lauryl sulphate, ammonium laureth sulphate, potassium laureth sulfate, sodium tridecyl benzene sulfonate, sodium dodecyl benzene sulfonate, sodium xylene sulfonate, monoethanolamine lauryl sulfate, monoethanolamine laureth sulfate, triethanolamine lauryl sulfate, triethanolamine laureth sulfate, lauryl sarcosine, cocoyl sarcosine, sodium lauryl sarcosinate, sodium lauroyl sarcosinate, triethylamine lauryl sulfate, triethylamine laureth sulfate, diethanolamine lauryl sulfate, diethanolamine laureth sulfate, lauric monoglyceride sodium sulfate, ammonium cocoyl sulfate, ammonium lauroyl sulfate, sodium cocoyl sulfate, sodium lauroyl sulfate, sodium cocoyl isethionate, potassium cocoyl sulfate, potassium lauryl sulfate, monoethanolamine cocoyl sulfate, monoetha nolamine lauryl sulfate, triethanolamine lauryl sulfate, sodium hydroxyethyl-2-decyl ether sulfates, sodium methyl-2-hydroxydecyl ether sulfates, sodium hydroxyethyl-2-dodecyl ether sulfates, sodium monoethoxylated lauryl alkyl sulfates, C12-C18 alkyl sulfonates, ethoxylated or native linear and ramified C12-C18 alcohol sulfates, ethoxylated or native linear and ramified C12-C18 alcohol sulfates, and mixtures thereof.

Typical cationic surfactants include but are not limited to quaternary ammonium salts having one or two alkyl chain comprising 10 to 22 carbon atoms, and optionally hydroxyl groups, and two to three alkyl groups having 1 to 4 carbon or hydroxyalkyl or hydroxyl groups, or alkoxy groups, having typically about 1 to about 10 ethylene oxide moieties, and an anion selected from the group of halides, hydroxides, acetates and methylsulfate, such as ditallowalkyldimethyl (or diethyl or dihydroxyethyl) ammonium chloride, ditallowalkyldimethylammonium methyl sulfate, methyl tallowalkyl amido ethyl, ditallowalkyldimethylammonium methyl sulfate, dihexadecylalkyl dimethyl (or diethyl, or dihydroxyethyl) ammonium chloride, dioctadecyl-alkyl dimethylammonium chloride, such as DODMAC (dioctadecyl dimethyl ammonium chloride), and dieicosylalkyl dimethylammonium chloride, ethyl-tallowalkyl imidazolinium methyl sulphate, ditallowalkyldimethylammonium methyl sulfate, methyl tallowalkyl amido ethyl tallowalkyl imidazolinium methyl sulfate, quaternary ammonium salts having one or two acyloxy-alkyl chains, one or two alkyl groups and/or one or two hydroxyalkyl groups, such as so-called esterquat (N-methyl-N,N,bis[2-(C 16-C18-acetoxy)ethyl)]-N-(2-hydroxyethyl) ammonium methosulfate), diesterquat (N,N,N-trimethyl-N-[1,2-di-(C16-C18-acyloxy)propyl ammonium salts), DEEDMAC (N,N-dimethyl-N,N-bis([2-(-[(1-oxooctadecyl)oxy]ethyl) ammonium chloride, HEQ (N,N,N-trimethyl-N—[(Z)-2-hydroxy-3-[(1-oxo-octadec-9-enyl)oxy]] ammonium chloride, TEAQ (diquaternized methylsulfate salt of the reaction product between C10-C20 staturated and unsaturated fatty acids and triethanoloamine), alkylbenzyl dialkyl ammonium chloride, whereas the anion is selected from halides (such as chloride or bromide), hydroxy, ethylsulfate, acetate, carbonate, nitrate, phosphate and methylcarbonate.

Typical cationogenic surfactants include but are not limited to primary, secondary and tertiary amines, and ethoxylated fatty amines, such as lauriminopropyldimethyl amine, lauriminoethyldimethyl amine, myristyl amine, tridecyl amine, N-oleyl-1,3-propane diamine, ethoxylated N-tallow-1,3-propanediamine.

Typical zwitterionic surfactants include but are not limited to derivatives of aliphatic quaternary ammonium, phosphonium, and sulfonium compounds having linear or ramified alkyl, or alkenyl, or hydroxyl alkyl or alkoxy radicals, one of which having from about 8 to about 18 carbon atoms and another of which containing an anionic group selected from carboxyl, sulfonate, sulfate, succinate, phosphate or phosphonate groups. The alkoxy radicals include typically about 1 to about 10 ethylene oxide moieties or about 1 to about 3 glyceryl moieties. The hydroxyl alkyl radicals comprise typically alkylol moieties having 1 to 3 carbon atoms. A particular class of zwitterionic surfactant includes betaines comprising a quaternized cationic ammonium group and an anionic carboxylate group, separated by at least one methylene group, such as coco dimethylcarboxymethyl betaine, lauryl dimethyl carboxymethyl betaine, lauryl dimethyl alpha-carboxyethyl betaine, cetyl dimethyl carboxymethyl betaine, oleyl dimethyl gamma-carboxypropyl betaine, lauryl and stearyl bis-(2-hydroxyethyl) carboxymethyl betaine, oleyl dimethyl gamma-carboxypropyl betaine, and lauryl bis-(2-hydroxypropyl)-alpha-carboxyethyl betaine. Other betaines include amidoalkyl, sulfoalkyl and alkyl amidosufo betaines, wherein the alkyl moiety is typically an ethyl or a propyl moiety, such as cocoamidopropyl betaine, cocodimethylsulfopropyl betaine, lauryl dimethyl sulfoethyl betaine, lauryl bis-(2-hydroxyethyl) sulfopropyl betaine and the like.

Typical amphoteric surfactants include but are not limited to derivatives of primary, secondary and tertiary amines having linear or ramified alkyl or alkenyl radicals, one of which having from about 8 to about 18 carbon atoms and another of which containing an anionic group selected from carboxyl, sulfonate, sulfate, succinate, phosphate or phosphonate groups, such as sodium 3-dodecylimino propionate, sodium 3-dodecyliminopropane sulfonate.

Non-ionic surfactants include but are not limited to C4-C22 alkyl ethoxylates with about 1-25 ethylene oxide units, including the so-called narrow peaked alkyl ethoxylates, particularly ethoxylates and mixed ethoxylates/propoxylates, alkyl dialkyl amine oxides, alkyl polyglycosides, alkanoyl glucose amides, and mixtures thereof. Specific examples of non-ionic surfactants are the condensation products of aliphatic alcohols with from about 1 to about 22 moles of ethylene oxide. The alkyl chain of the aliphatic alcohol can either be straight or branched, primary or secondary, and generally contains from about 8 to about 18 carbon atoms, preferably C8 to C18 (e.g. C10) with 2 to 14 moles of ethylene oxide, such as the condensation product of C11-C15 linear secondary alcohol with 9 moles ethylene oxide, or the condensation product of C12-C14 primary alcohol with 6 moles ethylene oxide, or the condensation product of C14-C15 linear alcohol with 4 moles of ethylene oxide, or the condensation product of C13-C15 alcohol with 9 moles ethylene, or the condensation products of C13 alcohols and 2-21 moles of ethylene oxide. This category of non-ionic surfactant is referred to generally as "alkyl ethoxylates."

Other examples of non-ionic surfactants include the condensation products of ethylene oxide with a hydrophobic base formed by the condensation of propylene oxide with propylene glycol (e.g. PPG-1-PEG-9 Lauryl Glycol Ether).

Further examples of non-ionic surfactants are the polyethylene glycol sorbitol ethers containing 3-30 EO units (including, for example, sorbitol esters with oleic, myristic, stearic, palmitic acid, and the like).

Further examples of non-ionic surfactants are the condensation products of ethylene oxide (EO) with the product resulting from the reaction of propylene oxide and ethylene diamine.

Semi-polar non-ionic surfactants are a special category of non-ionic surfactants which include water-soluble amine oxides. These amine oxide surfactants in particular include C10-C18 alkyl dimethyl amine oxides and C8-C12 alkoxy ethyl dihydroxy ethyl amine oxides, such as NN-dihydroxyethyl-N-stearamine oxide, ethoxylated lauramide and lauryldimethylamine oxide.

Other non-ionic surfactants are alkyl polyglycosides including, for example, C8-C10 polyglycosides, such as C12-C16 alkyl polyglycosides, C8-C16 alkyl polyglycosides, C5 Amyl xyloside) and mixture of C5 Amyl, C8 Capryl, C12 Lauryl. The term "alkyl" as used hereinabove for the non-ionic sugar-based surfactant refers to saturated linear alkyl residues having 3 to 21 carbon atoms, including hexyl, octyl, decanyl, dodecanyl, tetradecanyl, hexadecanyl, and octadecanyl.

Further non-ionic surfactants include, for example, PEG 40 or PEG 400 hydrogenated castor oil.

Further non-ionic surfactants include glycerol-based surfactants having alkyl, alkenyl or hydroxyalkenyl residues having 5 to 21 carbon atoms, and different numbers of glyceryl moieties, such as octanoic acid hexaglyceryl ester, decanoic acid tetraglyceryl ester, riccinoleic acid hexaglyceryl ester, cocoic acids tetraglyceryl esters, and mixture thereof.

The consumer products concerned by the present invention may include acids or bases, or substances providing acidity or alkalinity, also referred to as acidity sources or alkalinity sources. The acids or acidity sources may be inorganic or organic. Inorganic acids and acidity sources may include hydrochloric acid, sulfuric acid, sulfamic acid, phosphoric acids and the like. Organic acids or acidity sources may include benzoic acid, citric acid, malic acid, and the like. The bases or alkalinity sources may also be inorganic or organic. Inorganic bases and alkalinity sources may include sodium hydroxide, ammonia, and salts comprising carbonates, phosphates, and the like.

The consumer products concerned by the present invention may include builders for reducing water hardness, such as phosphates, polyphosphates, polycarboxylates, sodium citrate, sodium carbonate, sodium silicate, sodium aluminosilicate (zeolite), and the like.

In many cases, the consumer products concerned by the present invention are liquid and may include further additives, such as solvents, fillers, texturing agents, such as thickener and rheological aids, distributing aids, anti-redeposition agents, preservative agents, deodorizing agents, cosmetic active ingredients, surface enhancing agents, In a particular embodiment of the present invention is provided a consumer product comprising a compacted perfume composition and at least one solvent selected from water-soluble solvents, or water-insoluble, or partially water-soluble solvents.

Water-soluble co-solvents include, but are not limited to, ethanol, 1-propanol, 2-propanol, 1-butanol, 1,2-propane diol, 1,3-propane diol, 1,2-butanediol, 1,2-pentandiol 1,2-hexanediol, 1,2-heptanediol, 2-methyl-pentan-2,4-diol, carbitol, glycol ethers, such as propylene glycol, dipropylene glycol, 1,3-propanediol, glycol esters and glycol ethers, such as dipropylene glycol methyl ether acetate, dipropylene glycol methyl ether, propylene glycol n-butyl ether, diethylene glycol butyl ether, hexylene glycol, methyl methoxy butanol, (+/−)-2,2-dimethyl-4-hydroxymethyl-1,3-dioxolane, glycerine, dimethyl isosorbide, triethyl citrate and mixtures thereof.

Water-insoluble or partially insoluble solvents include, but are not limited to, isopropyl myristate, methyl myristate, alkyl esters, such as methyl linoleate, methyl palmitate, ethyl laurate, ethyl linoleate, ethyl oleate, ethyl octanoate, dibenzyl ether and diethyl phtalate, dibasic ester DBE (blend composed of diisobutyl glutarate, diisobutyl succinate, and diisobutyl adipate, commercially available from Solvay, or blend composed of diisobutyl glutarate, and diisobutyl adipate, commercially available from Invista, and hydrocarbons.

In a particular embodiment of the present invention there is provided a consumer product comprising the compacted perfume composition and at least one texturing agent and/or colloid stabilizer, selected from rheology modifiers, thickener, gel-forming agents, thixotropic agents, and dispersing agents.

These texturing agents and/or colloid stabilizers are typically water soluble of partially water soluble, or surface active polymers. These polymers include, but are not limited to quaternized hydroxyethyl cellulose, poly(diallyl ammonium chloride-co-acrylamide), quaternized guar gum, poly(acrylamidopropyltrimethyl ammonium chloride-co-acrylamide) copolymers, poly(methacrylamidopropyltrimethyl ammonium chloride), polyethyleneimine, poly[(3-methyl-1-vinylimidazolium methyl sulfate)-co-(1-vinylpyrrolidone, cationic polyamines, cationic polyacrylamide, poly(trimethylaminoethyl methacrylate), poyl(vinylamine, poly(dimethyldiallyl ammonium chloride), also called poly(DADMAC), chitosan, carboxymethyl cellulose, xanthan gum, acacia gum, ghatti gum, tragaganth gum, Arabic gum, sodium alginate, ethoxylated alginate, gelatine, dextran, hydroxythyl cellulose, hydroxypropyl cellulose, hydroxypropyl methylcellulose, poly(ethylene oxide), poly(ethylene oxide-b-propylene oxide) block-copolymers, polyacrylamide, polyacrylic acid or carbomers, sodium polyacrylate, acrylates copolymer, acrylates crosspolymer-4, acrylates crosspolymer-3, polyacrylate-2 crosspolymer, and polyacrylate-14, crosslinked acrylates/C10-30 alkyl acrylate copolymers, polyvinyl alcohol, polyvinyl pyrrolidone, pectin, and modified.

In a particular embodiment of the present invention is provided a consumer product, for example a hair care product, comprising the compacted perfume composition and at least one silicone, selected from, but not limited to dimethicone, poly(dimethylsiloxane), amino-silicone, such as amodimethicone, trialkylammonium-silicone salts, ethoxylated silicones and the like.

In a particular embodiment of the present invention is provided a consumer product comprising the compacted perfume composition and at least one active cosmetic ingredient selected from, but not limited to emollients, moisturizing agents, anti-wrinkle agents, exfoliating agents, sunscreen agents, dyes, pigments, talcum, conditioning agents, hair styling agents, and antidandruff agents.

In a particular embodiment of the present invention is provided a consumer product comprising a compacted perfume composition and at least one fabric enhancing agent, selected from, but not limited to softening agents, optical brighteners and antistatic agents.

In a particular embodiment of the present invention is provided a consumer product comprising a compacted perfume composition and at least one preservative selected from, but not limited to butylated hydroxyanisole (BHA), butylated hydroxytoluene (BHT), dilauryl thiodipropionate, alkyl parabene, tocopherols and the like. In another embodiment, a suitable preservative includes a combination of benzisothiazolone (BIT), methylisothiazolone (MIT) and/or laurylamine dipropylenediamine (BDA), and mixtures thereof, and mixtures of NN'-dihydroxymethyl urea and 1,6-dihydroxy-2,5-dioxo-hexane.

In a particular embodiment of the present invention is provided a consumer product comprising a compacted perfume composition and at least one deodorizing agent selected from, but not limited to zinc derivatives, essential oils, sodium undecylenate, methyl undecylenate, 2-hydroxypropyl beta cyclodextrin, soyethyl morpholiniu methosulfate, crotonates and fumarates, and alkylene carbonates.

In a particular embodiment of the present invention is provided a consumer product, for example home care products, comprising the compacted perfume composition and at least one solubilized, water soluble uncomplexed cyclodextrin selected from, but not limited to alpha-cyclodextrin, beta-cyclodextrin, gamma cyclodextrin and/or their derivatives, and/or mixture thereof. Cyclodextrin derivatives include, but are not limited to methoxy, ethoxy cyclodextrins, hydroxyl ethyl cyclodextrins, hydroxypropyl cyclodextrins, cationic cyclodextrins, such as 2-hydroxy-3-(trimethylammonium) propyloxy cyclodextrins, anionic cyclodextrins, such as carboxymethyl cyclodextrins and cyclodextrin sulfates and the like.

In one embodiment of the present invention, the consumer product is an all-purpose cleaner (APC) comprising typically from about 0.05 to about 25% by weight or, preferably from about 0.1 to about 20% by weight or preferably from about 1 to about 3% by weight of anionic and non-ionic surfactant, preferably selected from, but not limited to sodium alkyl sulfonates and alkyl ethoxylates; from about 1 to about 10 wt %, preferably from about 2 to about 6% by weight soaps, for example sodium fatty acid carboxylates; from about 1 to about 15% by weight, preferably from about 2 to about 10% by weight of alkalinity sources, for example sodium carbonate; from about 1 to about 10% by weight inorganic builders, for example sodium citrate—citric acid mixture; from about 0 to about 2% by weight organic builders, for example sodium polycarboxylate from about 0.0001 to about 0.5% by weight, preferably from about 0.0003 to about 0.1% by weight of one or more preservative(s); and, optionally, up to about 5% by weight of one or more water-soluble solvent(s), citric acid, triethanolamine, sodium hydroxide, potassium hydroxide, ammonia, and/or oils, and the compacted perfume composition in 0.01 to 0.75% by weight, more particularly from about 0.05 to 0.5% by weight and still more particularly from about 0.1 to 0.25% by weight.

In another embodiment of the present invention, the consumer product comprising the compacted perfume composition is a shampoo comprising typically from about 3% to 25% by weight, for example from about 12% to about 20% by weight or from about 14% to 18% by weight of one or more anionic surfactant(s); from about 0.5% to about 20% by weight, for example from about 1% to 10% by weight of zwitterionic and/or amphoteric surfactants; from 0% to about 10% by weight on non-ionic surfactants; from about 20% to about 90% by weight of an aqueous phase, comprising optionally water-soluble solvents; from about 0.0001 to about 0.5% by weight, preferably from about 0.0003 to about 0.1% by weight of one or more preservative(s); and optionally benefit agents, such as moisturizers, emollients, thickeners, anti-dandruff agents, hair growth promoting agents, vitamins, nutrients, dyes, hair colorants, and the like. The compacted perfume composition is present in 0.01 to 0.75% by weight, more particularly from about 0.05 to 0.5% by weight and still more particularly from about 0.1 to 0.25% by weight.

In a further embodiment of the present invention, the consumer product comprising the compacted perfume composition is a powder or a granulated detergent comprising typically 5 to 40% by weight of anionic surfactants, such as alkylbenzene sulphonates, alkylbenzene sulphonic acid and alkyl ethoxy sulfates, 4 to 15% by weight of non-ionic surfactants, such as alkyl alcohol ethoxylates, 10 to 60% builders, such as sodium carbonate, aluminosilicates, inorganic phosphates, citrates and polycarboxylates; and other ingredients, such as fillers, hydrotopes, humectants, bleach, enzymes, fabric softening agents, anti-wrinkle agents, fluorescent agents, and anti-redeposition polymers. The compacted perfume composition is present in 0.01 to 0.75% by weight, more particularly from about 0.05 to 0.5% by weight and still more particularly from about 0.1 to 0.25% by weight. The granulated detergent formulation may be in the form of beads, pellets or flakes.

In a further embodiment of the present invention, the consumer product comprising the compacted perfume composition further comprises microcapsules comprising an encapsulated perfume, whereas the micro-capsules are core-shell micro-capsules, water-insoluble matrix particles or water-soluble matrix particles and whereas the encapsulating material comprises at least one polymer selected from water-insoluble polymers, water-soluble polymers and polymers being partially soluble in water, selected from aminoplast resins, poly(meth)acrylates, poly(alkyl (meth)acrylate-co-(meth)acrylic acid), polyurea, polyurethane, polysulfones, polyesters, polyamides, poly(vinyl alcohol), proteins and carbohydrates. The encapsulated perfume may be a non-compacted perfume composition or a compacted perfume composition. The encapsulated perfume can be different or identical to the not encapsulated compacted perfume composition. In a particular embodiment, the compacted perfume composition according to the present invention is not encapsulated and the ratio of encapsulated to non-encapsulated perfumes is from 0.05 to 10, preferably from 0.1 to 1 and more preferably from 0.15 to 0.5.

In another embodiment, the compacted perfume composition is encapsulated in a plurality of microcapsules, whereas the micro-capsules are core-shell micro-capsules, water-insoluble matrix particles or water-soluble matrix particles and whereas the encapsulating material comprises at least one polymer selected from water-insoluble polymers, water-soluble polymers and polymers being partially soluble in water, selected from aminoplast resins, poly (meth)acrylates, poly(alkyl (meth)acrylate-co-(meth)acrylic acid), polyurea, polyurethane, polysulfones, polyesters, polyamides, poly(vinyl alcohol), proteins and carbohydrates. The consumer product comprising the encapsulated compacted perfume composition can further comprise a not encapsulated perfume composition (free oil), which might be a non-compacted perfume composition or a compacted perfume composition.

In order to further illustrate the present invention and the advantages thereof, the following specific examples and comparative example are given, it being understood that same are intended only as illustrative and non-limiting.

EXAMPLE 1

Table 1 provides a list of non-compacted and compacted perfume compositions. All percentages are given by weight of the total perfume composition. Under "Markers" is meant the total percentage of Performance Markers A1 in the perfume compositions. Under "Vehicles" is meant the total percentage of Performance Vehicles A2 in the perfume compositions. Under "Diluents" is meant the total percentage of Performing Diluents B1 in the perfume compositions. Under "Low Odour Ingredients" is meant the total percentage of solvents and low odour ingredients having an Odour Value of less than 100 in the perfume. Under "# Over critical Markers" is meant the total number of Performance Markers A1 being present at a concentration which is equal to or higher than their specific Critical Compaction Concentration. "NC" means not compacted; "TDC" means compacted via a top-down creation process; "BUC" means compacted via a bottom-up creation process according to the present invention.

TABLE 1

| Perfume | Total % of Performance Markers | Total % of Performance Vehicles | Total % of Performing Diluents | Total % of Other fragrance ingredients | Total % of Low Odour Ingredients | # Over-critical Markers |
| --- | --- | --- | --- | --- | --- | --- |
| A (NC) | 0.04 | 0.36 | 53.2 | 26.9 | 19.5 | 0 |
| B (TDC) | 0.4 | 2.5 | 65.1 | 32.0 | 0 | 0 |
| C (NC) | 0.1 | 6.6 | 68.9 | 20.8 | 3.6 | 0 |
| D (TDC) | 0.5 | 19.8 | 40.5 | 39.2 | 0 | 1 |
| E (NC) | 0.1 | 6.4 | 54.6 | 33.2 | 5.7 | 0 |
| F (BUC) | 3.1 | 25.6 | 49.0 | 21.7 | 0.6 | 3 |
| G (BUC) | 4.8 | 46.6 | 19 | 29.6 | 0 | 3 |
| H (BUC) | 6.3 | 24.6 | 40.9 | 28.2 | 0 | 7 |
| I (BUC) | 2.7 | 60.4 | 26.6 | 10.3 | 0 | 3 |

In the above table, Perfume B is a compacted version of Perfume A (having a musky woody character) in which the solvents (Low Odour Ingredients) have been replaced mostly by Performing Diluents (top-down creation process). However, the concentration of both Performance Markers and Performance Vehicles is under-critical and the compacted version has lost in bloom intensity.

Perfume D is a compacted version of Perfume C (having a sweet-woody-chypre character), also obtained through a top-down process. In this case, part of the performing diluents has been replaced by more powerful Performance Vehicles. Nevertheless, the concentration of Performance Markers is still under-critical and the blooming performance of the perfume is not acceptable. Perfume D has only one Performance Marker at over-critical concentrations: Cyclogalbanate (1%).

Perfume E was a perfume having strong citrus-floral character, characterized by a high level of orange essence, terpenic alcohols, hedione and woody/musky ingredients. This perfume could not be compacted using a top-down creation process without a complete loss of the citrusfloral odour direction.

Conversely, Perfumes F (a strong citrus-floral perfume) and G (a fruity-floral perfume) have been obtained through a bottom-up creation process, according to the present invention. Perfume F comprised the following Performance Markers A1 at over-critical concentrations: (E)-undec-9-enal (0.1%), Rose oxide (1%) and Spirogalbanone (0.4%), and Perfume G comprised following Performance Markers A1 at over-critical concentrations: Aldehyde C 11 undecylenic (1%), Rose oxide (0.7%) and Violet nirile (0.014%). Perfumes F and G are well balanced perfumes performing extremely from both a performance and hedonic stand points.

Perfumes H and I are further examples of compacted perfumes obtained by performing a bottom-up creation process in accordance with the invention: Perfume H is a strong fougère spicy oriental compacted perfume comprising following Performance Markers A1 at concentrations equal to or higher than their specific Critical Compaction Concentrations: Ambrocenide (0.05%), Damascenone (0.2%), Delta damascone (2%), Dupical (0.5%), Galbanone (0.5%), Methyl laitone (0.5%) and Shisolia (0.5%). Perfume I is a floral carnation compacted perfume comprising following Performance Markers at over-critical concentrations: Cetone V (1%), Trans-dec-4-enal (0.6%) and Rosyrane Super (0.25%).

EXAMPLE 2

Performance evaluation. A series of compacted perfume compositions created according to the method and composition rules defined by the present invention were evaluated in use in a hard surface cleaner product.

The base was a model base comprising 2% by weight of C14-17 secondary alkyl sulfonate (Hostapur® SAS 60, ex Clariant), 2% by weight of C13 ethoxylate (Lutensol® TO 10, ex BASF), 1% by weight of triethanolamine (ex Prolabo), 0.3% by weight of citric acid (ex Prolabo), 0.2% by weight of sodium hydroxide at 50% in dionized water (ex Prolabo) and 0.1% by weight of a mixture of NN'-dihydroxymethyl urea and 1,6-dihydroxy-2,5-dioxo-hexane (Parmetol® DF 35, ex Schulke & Mayr).

The level of compacted perfume composition in the product was 0.18% by weight, whereas the level of a reference un-compacted perfume composition was 0.5% by weight. The performance of the perfume compositions in terms of smell intensity (or perfume strength) was assessed in a monadic in-home use test under domestic application conditions. The quantity of product tested was 500 ml. The product was tested three times within 10 days. The number of panellists was 85. The results are reported in Table 2.

TABLE 2

| | Non compacted perfume J @ 0.5% | Compacted perfume K @0.18% | Compacted perfume L @0.18% |
|---|---|---|---|
| Composition(*) | | | |
| Performance Markers A1 (%) | 0.9 | 9.5 | 4.5 |
| Performance Vehicles A2 (%) | 8 | 12.5 | 27.4 |
| Performing Diluents B1 (%) | 37.0 | 31.0 | 24.8 |
| Other fragrance ingredients (%) | 47.0 | 46.0 | 40.8 |

TABLE 2-continued

| | Non compacted perfume J @ 0.5% | Compacted perfume K @0.18% | Compacted perfume L @0.18% |
|---|---|---|---|
| Low Odour Ingredients (%) | 7.1 | 1 | 2.5 |
| # Over-critical Markers(**) | 0 | 5 | 4 |
| Performance assessment stage(***) | | | |
| On neat product | 47% | 63% | 64% |
| Bloom under dilution with water | 72% | 85% | 79% |
| During use | 76% | 86% | 78% |
| 2 hours after application | 42% | 52% | 41% |
| 24 hours impact (substantivity) | 24% | 26% | 22% |

(*)in % by weight of the total perfume composition
(**)number of Performance Markers with a concentration equal to or higher than its specific Critical Compaction Concentration, respectively
(***)percentage of panellist judging that the strength of the perfume at assessment stage is at the right intensity The compacted perfume K contained the following Performance Markers A1 at concentrations equal to or above their CCC: Tridecenonitrile ((E)-tridec-2-enenitrile, 4.5%), trans-dec-4-enal (0.9%), Cassyrane (0.9%), Galbanone (0.7%), and 3,5,5-trimethylhexanal (0.7%).

The compacted perfume L comprised Performance Markers A1 at over-critical concentrations equal to or above their CCC: Delta damascone (1.8%), Dupical (0.9%), trans-dec-4-enal (0.9%), Pharaone (0.14%).

EXAMPLE 3

Two perfumes were tested in both conventional and compacted granulated detergent compositions. Perfume M was a non-compacted green-floral accord comprising terpene alcohols and nitriles, Iso E super, Lilial, Gardenol, Aubepine para cresol, Jasmacyclene, Peonile and Undecavertol, and Perfume N its compacted variant. The characteristics of these two perfumes are reported in Table 3. The two detergent compositions were evaluated in a monadic sequential in home consumer test. The size of the test was 150 panellists. The test conditions and the results on a scale of 7, 7 being the maximal score, are also reported in Table 3.

TABLE 3

| | Non Compacted perfume M | Compacted perfume N |
|---|---|---|
| Composition(*) | | |
| Performance Markers (%) | 2.8 | 4.0 |
| Performance Vehicles (%) | 19.2 | 19.8 |
| Performing Diluents (%) | 43.7 | 40.4 |
| Other fragrance ingredients (%) | 34.3 | 35.8 |
| Low odour ingredients (%) | 0 | 0 |
| # Over-critical Markers(**) | 0 | 5 |
| Detergent | Conventional | Compacted |
| Detergent dosage in machine wash test (g) | 150 | 30 |
| Perfume dosage in detergent (%) | 0.75 | 0.75 |
| Consumer testing results | | |
| Overall opinion of the perfume | 5.7 | 6.0 |
| Overall opinion of product efficiency | 5.6 | 5.9 |

(*)in % by weight of the total perfume composition
(**)number of Performance Markers with a concentration equal to or higher than its specific Critical Compaction Concentration, respectively.

As apparent from the results of Table 3, the compacted perfume N was rated higher by the panellists at a dosage 5 times lower than that of the non compacted perfume M. This example illustrates the importance of having in a compacted perfume at least three Performance Markers being at a level higher than or equal to their Critical Compaction Concentration.

EXAMPLE 4

A compacted perfume O was created comprising 5.2% by weight of Performance Markers A1, 68.6% by weight of Performance Vehicles A2 (Ethyl Maltol, Nectaryl, Petalia, Undecavertol) and 26.2% by weight of Performing Diluents B1 (Agrumex, Citrus essence, Orange essence). This perfume did not contain any additional perfume ingredient and did not contain any low odour ingredient. The compacted perfume O comprised seven Performance Markers A1 at concentrations equal to or above their CCC: Cassyrane (0.5%), Dupical (1.0%), Galbanone (1.0%), Javanol (1%), Oxane (0.75%), Rose Oxide (0.5%) and Thiogeraniol (0.1%).

EXAMPLE 5

A compacted perfume P was created comprising 7.8% by weight of Performance Markers A1, 35.30% by weight of Performance Vehicles A2 (Ethyl Maltol, Nectaryl, Petalia, Undecavertol) and 23.75% by weight of Performing Diluents B1 (Agrumex, Citrus essence, Orange essence). The compacted perfume P comprised 14 Performance Markers A1. From these 14 Performance Markers, 9 had concentrations equal to or above their CCC: Aldehyde C12 MOA (0.4%), Bigaryl (0.06%), Damascone Delta (1.6%), Dupical (1.6%), Evernyl (0.8%), Galbanone (0.27.0%), Javanol (0.40%), Pyralone (0.27%), Rose Oxide (1.2%) and Violet nitrile (0.016%).

The invention claimed is:
1. A compacted perfume composition comprising:
a) at least three Performance Markers A1, each of them at a level higher than or equal to the concentration given in parentheses, respectively, the total concentration of said Performance Markers A1 being higher than 1% by weight of the compacted perfume composition, wherein the Performance Markers A1 are selected from the group consisting of (2-(1-propoxyethoxy)ethyl) benzene (0.25%); acetophenone (0.6%); 1-(pyrazin-2-yl)ethanone (0.1%); 2,6,10-trimethylundec-9-enal (0.25%); 2-methyldecanal (0.5%); undec-10-enal (0.7%); hexanal (0.55%); heptanal (0.15%); 3,5,5-trimethylhexanal (0.45%); (E)-undec-9-enal (0.75%); 3,8,8,11a-tetramethyldodecahydro-1H-3,5a-epoxynaphtho[2,1-c]oxepine (0.05%); 1,3,4,5,6,7-hexahydro-.beta.,1,1,5,5-pentamethyl-2H-2,4a-methanonaphthalene-8-ethanol (0.15%); 2,5,5-trimethyl-1,2,3,4,4a,5,6,7-octahydronaphthalen-2-ol (0.1%); (4aR,5R,7aS,9R)-Octahydro-2,2,5,8,8,9a-hexamethyl-4h-4a,9-methanoazuleno[5,6-d]-1,3-dioxole (0.05%); oct-1-en-3-ol (0.2%); 7-isopentyl-2H-benzo[b][1,4]dioxepin-3(4H)-one (0.005%); 8-(sec-butyl)-5,6,7,8-tetrahydroquinoline, (0.01%); (1R,5S,E)-1,5-dimethylbicyclo[3.2.1]octan-8-one oxime (0.03%); 6-(sec-butyl)quinoline (0.1%); 7-methyl-2H-benzo[b][1,4]dioxepin-3(4H)-one (0.2%); 3-hydroxy-4,5-dimethylfuran-2(5H)-one (0.000075%); 5-isopropyl-2-methylphenol (0.4%); 5-tert-butyl-2-methyl-5-propyl-2H-furan (0.10%); (E)-1-(2,6,6-trimethylcyclohex-2-en-1-yl)hepta-1,6-dien-3-one (0.5%); 2-((3,7-dimethyloct-6-en-1-yl)oxy)acetaldehyde (0.2%); 2-(2-mercaptopropan-2-yl)-5-methylcyclohexanone (0.02%); (4S)-4,7,7-trimethyl-6-thiabicyclo[3.2.1]octane (0.3%); 2-(3-phenylpropyl)pyridine (0.015%); 2-hydroxy-3-methylcyclopent-2-enone (0.3%); p-tolyl octanoate (0.15%), 1-methoxy-4-methylbenzene (0.5%); 4-isopropylbenzonitrile (0.05%); 4-isopropylbenzaldehyde (0.2%); (E)-1-(2,6,6-trimethylcyclohexa-1,3-dien-1-yl)but-2-en-1-one (0.1%); (E)-1-(2,6,6-trimethylcyclohex-3-en-1-yl)but-2-en-1-one (0.3%); decanenitrile (0.3%); (E)-dec-2-enal (0.01%); (E)-dec-4-enal (0.1%); 9-decenal (0.05%); 2-(2-(3,3,5-trimethylcyclohexyl)acetyl)cyclopentanone (0.1%); (E)-dodec-2-enal (0.1%); (E)-4-((3aS,7aS)-hexahydro-1H-4,7-methanoinden-5(6H)-ylidene)butanal (0.15%); ethyl-3 dimethyl-2(5 or 6) pyrazine (0.03%); 8-ethyl-1-oxaspiro[4.5]decan-2-one (0.03%); methyl 2,4-dihydroxy-3,6-dimethylbenzoate (0.65%); (E)-undec-9-enenitrile (0.15%); methyl oct-2-ynoate (0.15%); 1-(3,3-dimethylcyclohex-1-en-1-yl)pent-4-en-1-one (0.2%); 2-methoxyphenol (0.05%); E-hex-2-enal (0.15%); 2-ethyl-4-hydroxy-5-methylfuran-3(2H)-one (0.1%); 2-phenylpropanal (0.25%); 2-isobutyl-3-methoxypyrazine (0.000005%); 2-isobutylquinoline (0.1%); (E)-2-methoxy-4-(prop-1-en-1-yl)phenol (0.7%); 6-isopropylquinoline (0.25%); 5-(sec-butyl)-2-(2,4-dimethylcyclohex-3-en-1-yl)-5-methyl-1,3-dioxane (0.55%); (3E,6E)-2,4,4,7-tetramethylnona-6,8-dien-3-one oxime (0.05%); bicyclo[2.2.2]oct-5-ene-2-carboxaldehyde (0.1%); 2-methoxy-3-methylpyrazine (0.2%); 2-hydroxy-3,4-dimethyl-2-cyclopenten-1-one (0.4%); 4,4,8a-trimethyldecahydronaphthalen-4a-ol (0.025%); 2-ethyl-4-methyl-1,3-thiazole (0.07%); 8-methyl-1-oxaspiro[4.5]decan-2-one (0.15%); methyl non-2-ynoate (0.1%); 10-isopropyl-2,7-dimethyl-1-oxaspiro[4.5]deca-3,6-diene (0.3%); (E)-methyl non-2-enoate (0.45%); 1-(3-methylbenzofuran-2-yl)ethanone (0.15%); (2E,6Z)-nona-2,6-dienal (0.02%); (Z)-non-6-enal (0.045%); 2-methyl-4-propyl-1,3-oxathiane (0.1%); 2-(4-methylcyclohex-3-en-1-yl)propane-2-thiol (0.0000065%); 5-methyl-2-(2-methylethyl)-cyclohexanone (0.01%); 2-cyclohexylhepta-1,6-dien-3-one (0.1%); 2-phenyl-ethanal (0.2%); (2E,5E)-5,6,7-trimethylocta-2,5-dien-4-one (0.05%); 6-(sec-butyl)quinoline (0.1%); dec-9-en-1-ol (0.4%); 4-methyl-2-(2-methylprop-1-en-1-yl)tetrahydro-2H-pyran (0.4%); 4-methylene-2-phenyltetrahydro-2H-pyran (0.10%); 2,3,3-trimethyl-2,3-dihydro-1H-inden-1-one (0.1%); 2,6,6-trimethylcyclohexa-1,3-dienecarbaldehyde (0.05%); 4-vinylcyclohex-1-enecarbaldehyde (0.15%); 1-spiro[4.5]dec-7-en-7-yl-4-penten-1-one (0.15%); 2-(p-tolyl)acetaldehyde (0.1%); (E)-3,7-dimethylocta-2,6-diene-1-thiol (0.05%); 4-methylbenzaldehyde (1%); 1-(cyclopropylmethyl)-4-methoxybenzene (0.10%); E-hex-2-enal (0.15%); (E)-tridec-2-enenitrile (0.1%); 3-phenylbutanal (0.5%); 2-ethoxy-4-methylphenol (0.15%); (3E,5Z)-undeca-1,3,5-triene (0.05%); (E)-undec-2-enal (0.1%); (E)-4-isopropyl-1-methyl-2-(prop-1-en-1-yl)benzene (0.25%); (2E,6Z)-nona-2,6-dienenitrile (0.01%); and 2-(2,4-dimethylcyclohexyl)pyridine (0.05%);
b) at least one Performance Vehicle A2, the total concentration of said Performance Vehicle A2 being higher than 10% by weight of the compacted perfume composition, wherein the Performance Vehicle A2 is selected from the group consisting of dodecanal; 2-methylundecanal; (Z)-oxacycloheptadec-10-en-2-one; 3a,6,6,9a-tetramethyldodecahydronaphtho[2,1-b]furan; 3a,6,6,9a-tetramethyldodecahydronaphtho[2,1-b]furan; (E)-1-methoxy-4-(prop-1-en-1-yl)benzene;

4-methoxybenzaldehyde; butyl butanoate; 6-methoxy-2,6-dimethyloctanal; (E)-3,7-dimethylocta-2,6-dienal; (E)-1,1-dimethoxy-3,7-dimethylocta-2,6-diene; (E)-1,1-diethoxy-3,7-dimethylocta-2,6-diene; (Z)-1,1-diethoxy-3,7-dimethylocta-2,6-diene; 3,7-dimethyloct-6-enal; 3,7-dimethyloct-6-enenitrile; 2,4,4,7-tetramethyloct-6-en-3-one; (Z)-3-methylcyclotetradec-5-enone; 2H-chromen-2-one; p-cresol; 8,8-dimethyl-1,2,3,4,5,6,7,8-octahydronaphthalene-2-carbaldehyde; 2,4,6-trimethylcyclohex-3-enecarbaldehyde; allyl 2-(cyclohexyloxy)acetate; (E)-1-(2,6,6-trimethylcyclohex-2-en-1-yl)but-2-en-1-one; 6-isopropyloctahydronaphthalen-2(1H)-one; 3-methyl-2-pentylcyclopent-2-enone; 1-methoxy-4-propylbenzene; 2-methoxy-4-propylphenol; 4,7-dimethyloct-6-en-3-one; (E)-3-methyl-5-(2,2,3-trimethylcyclopent-3-en-1-yl)pent-4-en-2-ol; 3-(1-ethoxyethoxy)-3,7-dimethylocta-1,6-diene; ethyl butyrate; 2-ethyl-3-hydroxy-4H-pyran-4-one; ethyl 2,6,6-trimethylcyclohexa-1,3-diene-1-carboxylate; 3-ethoxy-4-hydroxybenzaldehyde; ethyl 2-methylbutanoate; ethyl 2-hydroxybenzoate; 3-(3-isopropylphenyl)butanal; (3aR,6S,7aS)-3a,4,5,6,7,7a-hexahydro-1H-4,7-methanoinden-6-yl propionate; 3-methyldodecanenitrile; N,2-dimethyl-N-phenylbutanamide; (3aR,6S,7aS)-3a,4,5,6,7,7a-hexahydro-1H-4,7-methanoinden-6-yl isobutyrate; Geranium essence; 2-(2-hydroxypropan-2-yl)-5-methylcyclohexanol; 3-ethoxy-1,1,5-trimethylcyclohexane; 2-hexylcyclopent-2-enone; (E)-3-methyl-4-(2,6,6-trimethylcyclohex-2-en-1-yl)but-3-en-2-one; (3aR,6S,7aS)-3a,4,5,6,7,7a-hexahydro-1H-4,7-methanoinden-6-yl acetate; 2-hexylcyclopentanone; (1-methyl-2-((1,2,2-trimethylbicyclo[3.1.0]hexan-3-yl)methyl)cyclopropyl)methanol; (Z)-1-(1-ethoxyethoxy)hex-3-ene; (2E,6Z)-3,7-dimethylnona-2,6-dienenitrile; (Z)-hex-3-en-1-yl methyl carbonate; (E)-methyl 2-(((2,4-dimethylcyclohex-3-en-1-yl)methylene)amino)benzoate; 2-(5-methyl-5-vinyltetrahydrofuran-2-yl)propan-2-ol; ethyl 2-methylpentanoate; 3-methyl-5-phenylpentanal; 2,6-dimethylhept-5-enal; 1-(p-tolyl)ethanone; (E)-1,2-dimethoxy-4-(prop-1-en-1-yl)benzene; methyl 2-hydroxybenzoate; (Z)-3-methylcyclopentadec-5-enone; 2-(2-(4-methylcyclohex-3-en-1-yl)propyl)cyclopentanone; 2-ethyl-N-methyl-N-(m-tolyl)butanamide; Patchouli essence; 5-heptyldihydrofuran-2(3H)-one; 2-cyclohexylidene-2-phenylacetonitrile; 2-cyclohexylidene-2-(o-tolyl)acetonitrile; 3-(6,6-dimethylbicyclo[3.1.1]hept-2-en-2-yl)propanal; (3aR,6S,7aS)-3a,4,5,6,7,7a-hexahydro-1H-4,7-methanoinden-6-yl pivalate; (E)-3,3-dimethyl-5-(2,2,3-trimethyl-3-cyclopenten-1-yl)-4-penten-2-ol; 5-pentyldihydrofuran-2(3H)-one; 2-pentylcyclopentanone; (E)-2-ethyl-4-(2,2,3-trimethylcyclopent-3-en-1-yl)but-2-en-1-ol; 4-(4-hydroxyphenyl)butan-2-one; 2,4-dimethyl-4-phenyltetrahydrofuran; (2R,8aS)-3',6-dimethyl-3,4,4a,5,8,8a-hexahydro-1H-spiro[1,4-methanonaphthalene-2,2'-oxirane]; 3-isobutyl-1-methylcyclohexanol; methyl 2-((E)-((E)-2-benzylideneheptylidene)amino)benzoate; cyclopentadecanone and hexadecanolide; (E)-5-methylheptan-3-one oxime; (E)-2-((3,5-dimethylhex-3-en-2-yl)oxy)-2-methylpropyl cyclopropanecarboxylate; 1-(2,2,6-trimethylcyclohexyl)hexan-3-ol; 4-methylbenzaldehyde; (E)-4-methyldec-3-en-5-ol; 4-hydroxy-3-methoxybenzaldehyde; (E)-2-ethoxy-5-(prop-1-en-1-yl)phenol; (Z)-cyclohexadec-5-enone; 4-methyl-4-phenylpentan-2-yl acetate; 2-methoxynaphthalene; (4E)-9-hydroxy-5,9-dimethyl-4-decenal; 1-methyl-2-(5-methylhex-4-en-2-yl)cyclopropyl)-methanol; and 3-(4-isobutyl-2-methylphenyl)propanal; and c) at least one Performing Diluent B1, the total concentration of said Performing Diluent B1 being higher than 5% by weight of the compacted perfume composition, wherein the Performing Diluent B1 is selected from the group consisting of 2-(tert-butyl)cyclohexyl acetate; pentyl 2-hydroxybenzoate; propanedioic acid 1-(1-(3,3-dimethylcyclohexyl)ethyl) 3-ethyl ester; benzyl 2-hydroxybenzoate; (1S,4S)-1,7,7-trimethylbicyclo[2.2.1]heptan-2-one; 3,7-dimethyloct-6-en-1-ol; citrus essence; 3-(4-isopropylphenyl)-2-methylpropanal; cyclohexyl 2-hydroxybenzoate; methyl 1,4-dimethylcyclohexanecarboxylate; 1-oxacycloheptadecan-2-one; 3-methyl-2-pentylcyclopent-2-enone; 2,6-dimethyloct-7-en-2-ol; 2,6-dimethylheptan-2-ol; 2,6-dimethyloct-7-en-2-yl formate; 1-methyl-4-(prop-1-en-2-yl)cyclohex-1-ene; 1,4-dioxacycloheptadecane-5,17-dione; (1s,4s)-1,3,3-trimethyl-2-oxabicyclo[2.2.2]octane; 1-(3,5,5,6,8,8-hexamethyl-5,6,7,8-tetrahydronaphthalen-2-yl)ethanone; tetrahydro-4-methyl-2-(2-methylpropyl)-2H-pyran-4-ol; 2-(sec-butyl)cyclohexanone; 4,6,6,7,8,8-hexamethyl-1,3,4,6,7,8-hexahydrocyclopenta[g]isochromene; 1-phenylethyl acetate; 1-(1,2,8,8-tetramethyl-1,2,3,4,5,6,7,8-octahydronaphthalen-2-yl)ethanone; (E)-3,7-dimethylocta-2,6-dien-1-ol; (E)-oxacyclohexadec-12-en-2-one; methyl 3-oxo-2-pentylcyclopentaneacetate; 2-(1-(3,3-dimethylcyclohexyl)ethoxy)-2-methylpropyl propionate; (2 S)-ethyl 3-isopropylbicyclo[2.2.1]hept-5-ene-2-carboxylate; 2-butyl-4,4,6-trimethyl-1,3-dioxane; hexyl 2-hydroxybenzoate; 7-hydroxy-3,7-dimethyloctanal; (E)-4-(2,6,6-trimethylcyclohex-1-en-1-yl)but-3-en-2-one; 1-(2,3,8,8-tetramethyl-1,2,3,4,5,6,7,8-octahydronaphthalen-2-yl)ethanone; (4Z)-hept-4-en-2-yl 2-hydroxybenzoate; 3-(4-(tert-butyl)phenyl)-2-methylpropanal; linal oxide; 3,7-dimethylocta-1,6-dien-3-ol; (4-isopropylcyclohexyl)methanol; 6,6-dimethoxy-2,5,5-trimethylhex-2-ene; 1a,3,3,4,6,6-hexamethyl-1a,2,3,4,5,6,7,7a-octahydronaphtho[2,3-b]oxirene; 1,4-dioxacyclohexadecane-5,16-dione; cyclopentadecanone; 1,7-dioxacycloheptadecan-8-one; (E)-13-methyloxacyclopentadec-10-en-2-one; 2,4-dimethyl-2-(5,5,8,8-tetramethyl-5,6,7,8-tetrahydronaphthalen-2-yl)-1,3-dioxolane; orange essence; 4-(tert-butyl)cyclohexyl acetate; 2-phenylethanol; acetic acid (1-oxopropoxy)-, 1-(3,3-dimethylcyclohexyl)ethyl ester; 1-(3,3-dimethylcyclohexyl)ethyl acetate; (3S)-3,7-Dimethyloct-7-en-1-ol; 2-(1-(3,3-dimethylcyclohexyl)ethoxy)-2-methylpropyl cyclopropanecarboxylate; 3-(4-isobutylphenyl)-2-methylpropanal; (E)-6,10-dimethylundeca-5,9-dien-2-yl acetate; 3,7-dimethyloctan-3-ol; and oxacyclohexadecan-2-one, wherein the perfume composition comprises less than 3% by weight of low odour ingredients having an Odour Value of less than 100, and wherein the compacted perfume composition is adapted for use as a constituent for a compacted consumer product in an amount of between 0.01 to 0.75% by weight of the compacted consumer product.

2. The compacted perfume composition according to claim 1, further comprising at least one perfumery ingredient B2 belonging to none of the groups A1, A2 and B1 and having an Odour Value of 100 or more.

3. The compacted perfume composition according to claim 1, having a floral character.

4. The compacted perfume composition according to claim 1, wherein the compacted perfume composition is encapsulated.

5. A consumer product comprising the compacted perfume composition as defined in claim 1.

6. The consumer product according to claim 5, further comprising at least one solvent selected from water-soluble, water-insoluble and partially water-soluble solvents.

7. The consumer product according to claim 5, further comprising at least one texturing agent or colloid stabilizer, selected from the group consisting of rheology modifiers, thickeners, gel-forming agents, thixotropic agents and dispersing agents.

8. The consumer product according to claim 5, further comprising at least one compound selected from the group consisting of silicones, active cosmetic ingredients, fabric enhancing agents, preservatives, deodorizing agents, solubilized, and water soluble uncomplexed cyclodextrins.

9. The consumer product according to claim 5, further comprising at least one surfactant selected from the group consisting of anionic, cationic, cationogenic, zwitterionic, amphoteric and non-ionic surfactants.

10. A process of constructing compacted perfume compositions comprising the step of admixing:
a) at least three Performance Markers A1, each of them at a level higher than or equal to the concentration given in parentheses, respectively, the total concentration of said Performance Markers A1 being higher than 1% by weight of the compacted perfume composition, wherein the Performance Markers A1 are selected from the group consisting of (2-(1-propoxyethoxy)ethyl) benzene (0.25%); acetophenone (0.6%); 1-(pyrazin-2-yl)ethanone (0.1%); 2,6,10-trimethylundec-9-enal (0.25%); 2-methyldecanal (0.5%); undec-10-enal (0.7%); hexanal (0.55%); heptanal (0.15%); 3,5,5-trimethylhexanal (0.45%); (E)-undec-9-enal (0.75%); 3,8,8,11a-tetramethyldodecahydro-1H-3,5a-epoxynaphtho[2,1-c]oxepine (0.05%); 1,3,4,5,6,7-hexahydro-.beta.,1,1,5,5-pentamethyl-2H-2,4a-methanonaphthalene-8-ethanol (0.15%); 2,5,5-trimethyl-1,2,3,4,4a,5,6,7-octahydronaphthalen-2-ol (0.1%); (4aR,5R,7a S,9R)-Octahydro-2,2,5,8,8,9a-hexamethyl-4h-4a,9-methanoazuleno[5,6-d]-1,3-dioxole (0.05%); oct-1-en-3-ol (0.2%); 7-isopentyl-2H-benzo[b][1,4]dioxepin-3 (4H)-one (0.005%); 8-(sec-butyl)-5,6,7,8-tetrahydroquinoline (0.01%); (1R,5S,E)-1,5-dimethylbicyclo[3.2.1]octan-8-one oxime (0.03%); 6-(sec-butyl)quinoline (0.1%); 7-methyl-2H-benzo[b][1,4]dioxepin-3 (4H)-one (0.2%); 3-hydroxy-4,5-dimethylfuran-2(5H)-one (0.000075%); 5-isopropyl-2-methylphenol (0.4%); 5-tert-butyl-2-methyl-5-propyl-2H-furan (0.10%); (E)-1-(2,6,6-trimethylcyclohex-2-en-1-yl)hepta-1,6-dien-3-one (0.5%); 2-((3,7-dimethyloct-6-en-1-yl)oxy)acetaldehyde (0.2%); 2-(2-mercaptopropan-2-yl)-5-methylcyclohexanone (0.02%); (4 S)-4,7,7-trimethyl-6-thiabicyclo[3.2.1]octane (0.3%); 2-(3-phenylpropyl)pyridine (0.015%); 2-hydroxy-3-methylcyclopent-2-enone (0.3%); p-tolyl octanoate (0.15%); 1-methoxy-4-methylbenzene (0.5%); 4-isopropylbenzonitrile (0.05%); 4-isopropylbenzaldehyde (0.2%); (E)-1-(2,6,6-trimethylcyclohexa-1,3-dien-1-yl)but-2-en-1-one (0.1%); (E)-1-(2,6,6-trimethylcyclohex-3-en-1-yl)but-2-en-1-one (0.3%); decanenitrile (0.3%); (E)-dec-2-enal (0.01%); (E)-dec-4-enal (0.1%); 9-decenal (0.05%); 2-(2-(3,3,5-trimethylcyclohexyl)acetyl)cyclopentanone (0.1%); (E)-dodec-2-enal (0.1%); (E)-4-((3aS,7aS)-hexahydro-1H-4,7-methanoinden-5(6H)-ylidene)butanal (0.15%); ethyl-3 dimethyl-2(5 or 6) pyrazine (0.03%); 8-ethyl-1-oxaspiro[4.5]decan-2-one (0.03%); methyl 2,4-dihydroxy-3,6-dimethylbenzoate (0.65%); (E)-undec-9-enenitrile (0.15%); methyl oct-2-ynoate (0.15%); 1-(3,3-dimethylcyclohex-1-en-1-yl)pent-4-en-1-one (0.2%); 2-methoxyphenol (0.05%); E-hex-2-enal (0.15%); 2-ethyl-4-hydroxy-5-methylfuran-3(2H)-one (0.1%); 2-phenylpropanal (0.25%); 2-isobutyl-3-methoxypyrazine (0.000005%); 2-isobutylquinoline (0.1%); (E)-2-methoxy-4-(prop-1-en-1-yl)phenol (0.7%); 6-isopropylquinoline (0.25%); 5-(sec-butyl)-2-(2,4-dimethylcyclohex-3-en-1-yl)-5-methyl-1,3-dioxane (0.55%); (3E,6E)-2,4,4,7-tetramethylnona-6,8-dien-3-one oxime (0.05%); bicyclo[2.2.2]oct-5-ene-2-carboxaldehyde (0.1%); 2-methoxy-3-methylpyrazine (0.2%); 2-hydroxy-3,4-dimethyl-2-cyclopenten-1-one (0.4%); 4,4,8a-trimethyldecahydronaphthalen-4a-ol (0.025%); 2-ethyl-4-methyl-1,3-thiazole (0.07%); 8-methyl-1-oxaspiro[4.5]decan-2-one (0.15%); methyl non-2-ynoate (0.1%); 10-isopropyl-2,7-dimethyl-1-oxaspiro[4.5]deca-3,6-diene (0.3%); (E)-methyl non-2-enoate (0.45%); 1-(3-methylbenzofuran-2-yl)ethanone (0.15%); (2E,6Z)-nona-2,6-dienal (0.02%); (Z)-non-6-enal (0.045%); 2-methyl-4-propyl-1,3-oxathiane (0.1%); 2-(4-methylcyclohex-3-en-1-yl)propane-2-thiol (0.0000065%); 5-methyl-2(2-methylethyl)-cyclohexanone (0.01%); 2-cyclohexylhepta-1,6-dien-3-one (0.1%); 2-phenyl-ethanal (0.2%); (2E,5E)-5,6,7-trimethylocta-2,5-dien-4-one (0.05%); 6-(sec-butyl)quinoline (0.1%); dec-9-en-1-ol (0.4%); 4-methyl-2-(2-methylprop-1-en-1-yl)tetrahydro-2H-pyran (0.4%); 4-methylene-2-phenyltetrahydro-2H-pyran (0.10%); 2,3,3-trimethyl-2,3-dihydro-1H-inden-1-one (0.1%); 2,6,6-trimethylcyclohexa-1,3-dienecarbaldehyde (0.05%); 4-vinylcyclohex-1-enecarbaldehyde (0.15%); 1-spiro[4.5]dec-7-en-7-yl-4-penten-1-one (0.15%); 2-(p-tolyl)acetaldehyde (0.1%); (E)-3,7-dimethylocta-2,6-diene-1-thiol (0.05%); 4-methylbenzaldehyde (1%); 1-(cyclopropylmethyl)-4-methoxybenzene (0.10%); E-hex-2-enal (0.15%); (E)-tridec-2-enenitrile (0.1%); 3-phenylbutanal (0.5%); 2-ethoxy-4-methylphenol (0.15%); (3E,5Z)-undeca-1,3,5-triene (0.05%); (E)-undec-2-enal (0.1%); (E)-4-isopropyl-1-methyl-2-(prop-1-en-1-yl)benzene (0.25%); (2E,6Z)-nona-2,6-dienenitrile (0.01%); 2-(2,4-dimethylcyclohexyl)pyridine (0.05%);
b) at least one Performance Vehicle A2, the total concentration of said Performance Vehicles A2 being higher than 10% by weight of the compacted perfume composition, wherein the Performance Vehicles A2 are selected from the group consisting of dodecanal; 2-methylundecanal; (Z)-oxacycloheptadec-10-en-2-one; 3a,6,6,9a-tetramethyldodecahydronaphtho[2,1-b]furan; 3a,6,6,9a-tetramethyldodecahydronaphtho[2,1-b]furan; (E)-1-methoxy-4-(prop-1-en-1-yl)benzene; 4-methoxybenzaldehyde; butyl butanoate; 6-methoxy-2,6-dimethyloctanal; (E)-3,7-dimethylocta-2,6-dienal; (E)-1,1-dimethoxy-3,7-dimethylocta-2,6-diene; (E)-1,1-diethoxy-3,7-dimethylocta-2,6-diene; (Z)-1,1-diethoxy-3,7-dimethylocta-2,6-diene; 3,7-dimethyloct-6-enal; 3,7-dimethyloct-6-enenitrile; 2,4,4,7-tetramethyloct-6-en-3-one; (Z)-3-methylcyclotetradec-5-enone; 2H-chromen-2-one; p-cresol; 8,8-dimethyl-1,2,3,4,5,6,7,8-octahydronaphthalene-2-carbaldehyde;

l2,4,6-trimethylcyclohex-3-enecarbaldehyde; allyl 2-(cyclohexyloxy)acetate; (E)-1-(2,6,6-trimethylcyclohex-2-en-1-yl)but-2-en-1-one; 6-isopropyloctahydronaphthalen-2 (1H)-one; 3-methyl-2-pentylcyclopent-2-enone; 1-methoxy-4-propylbenzene; 2-methoxy-4-propylphenol; 4,7-dimethyloct-6-en-3-one; (E)-3-methyl-5-(2,2,3-trimethylcyclopent-3-en-1-yl)pent-4-en-2-ol; 3-(1-ethoxyethoxy)-3,7-dimethylocta-1,6-diene; ethyl butyrate; 2-ethyl-3-hydroxy-4H-pyran-4-one; ethyl 2,6,6-trimethylcyclohexa-1,3-diene-1-carboxylate; 3-ethoxy-4-hydroxybenzaldehyde; ethyl 2-methylbutanoate; ethyl 2-hydroxybenzoate; 3-(3-isopropylphenyl)butanal; (3aR,6S,7aS)-3a,4,5,6,7,7a-hexahydro-1H-4,7-methanoinden-6-yl propionate; 3-methyldodecanenitrile; N,2-dimethyl-N-phenylbutanamide; (3aR,6S,7aS)-3a,4,5,6,7,7a-hexahydro-1H-4,7-methanoinden-6-yl isobutyrate; geranium essence; 2-(2-hydroxypropan-2-yl)-5-methylcyclohexanol; 3-ethoxy-1,1,5-trimethylcyclohexane; 2-hexylcyclopent-2-enone; (E)-3-methyl-4-(2,6,6-trimethylcyclohex-2-en-1-yl)but-3-en-2-one; (3aR,6S,7aS)-3a,4,5,6,7,7a-hexahydro-1H-4,7-methanoinden-6-yl acetate; 2-hexylcyclopentanone; (1-methyl-2-((1,2,2-trimethylbicyclo[3.1.0]hexan-3-yl)methyl)cyclopropyl)methanol; (Z)-1-(1-ethoxyethoxy)hex-3-ene; (2E,6Z)-3,7-dimethylnona-2,6-dienenitrile; (Z)-hex-3-en-1-yl methyl carbonate; (E)-methyl 2-(((2,4-dimethylcyclohex-3-en-1-yl)methylene)amino)benzoate; 2-(5-methyl-5-vinyltetrahydrofuran-2-yl)propan-2-ol; ethyl 2-methylpentanoate; 3-methyl-5-phenylpentanal; 2,6-dimethylhept-5-enal; 1-(p-tolyl)ethanone; (E)-1,2-dimethoxy-4-(prop-1-en-1-yl)benzene; methyl 2-hydroxybenzoate; (Z)-3-methylcyclopentadec-5-enone; 2-(2-(4-methylcyclohex-3-en-1-yl)propyl)cyclopentanone; 2-ethyl-N-methyl-N-(m-tolyl)butanamide; patchouli essence; 5-heptyldihydrofuran-2(3H)-one; 2-cyclohexylidene-2-phenylacetonitrile; 2-cyclohexylidene-2-(o-tolyl)acetonitrile; 3-(6,6-dimethylbicyclo[3.1.1]hept-2-en-2-yl)propanal; (3aR,6S,7aS)-3a,4,5,6,7,7a-hexahydro-1H-4,7-methanoinden-6-yl pivalate; (E)-3,3-dimethyl-5-(2,2,3-trimethyl-3-cyclopenten-1-yl)-4-penten-2-ol; 5-pentyldihydrofuran-2(3H)-one; 2-pentylcyclopentanone; (E)-2-ethyl-4-(2,2,3-trimethylcyclopent-3-en-1-yl)but-2-en-1-ol; 4-(4-hydroxyphenyl)butan-2-one; 2,4-dimethyl-4-phenyltetrahydrofuran; (2R,8aS)-3',6-dimethyl-3,4,4a,5,8,8a-hexahydro-1H-spiro[1,4-methanonaphthalene-2,2'-oxirane]; 3-isobutyl-1-methylcyclohexanol; methyl 2-((E)-((E)-2-benzylideneheptylidene)amino)benzoate; cyclopentadecanone and hexadecanolide; (E)-5-methylheptan-3-one oxime; (E)-2-((3,5-dimethylhex-3-en-2-yl)oxy)-2-methylpropyl cyclopropanecarboxylate; 1-(2,2,6-trimethylcyclohexyl)hexan-3-ol; 4-methylbenzaldehyde; (E)-4-methyldec-3-en-5-ol; 4-hydroxy-3-methoxybenzaldehyde; (E)-2-ethoxy-5-(prop-1-en-1-yl)phenol; (Z)-cyclohexadec-5-enone; 4-methyl-4-phenylpentan-2-yl acetate; 2-methoxynaphthalene; (4E)-9-hydroxy-5,9-dimethyl-4-decenal; 1-methyl-2-(5-methylhex-4-en-2-yl)cyclopropyl)-methanol; and 3-(4-isobutyl-2-methylphenyl)propanal; and c) at least one Performing Diluent B1, the total concentration of said Performing Diluents B1 being higher than 5% by weight of the compacted perfume composition, wherein the Performing Diluent B1 are selected from the group consisting of 2-(tert-butyl)cyclohexyl acetate; pentyl 2-hydroxybenzoate; propanedioic acid 1-(1-(3,3-dimethylcyclohexyl)ethyl) 3-ethyl ester; benzyl 2-hydroxybenzoate; (1 S,4S)-1,7,7-trimethylbicyclo[2.2.1]heptan-2-one; 3,7-dimethyloct-6-en-1-ol; citrus essence; 3-(4-isopropylphenyl)-2-methylpropanal; cyclohexyl 2-hydroxybenzoate; methyl 1,4-dimethylcyclohexanecarboxylate; 1-oxacycloheptadecan-2-one; 3-methyl-2-pentylcyclopent-2-enone; 2,6-dimethyloct-7-en-2-ol; 2,6-dimethylheptan-2-ol; 2,6-dimethyloct-7-en-2-yl formate; 1-methyl-4-(prop-1-en-2-yl)cyclohex-1-ene; 1,4-dioxacycloheptadecane-5,17-dione; (1s,4s)-1,3,3-trimethyl-2-oxabicyclo[2.2.2]octane; 1-(3,5,5,6,8,8-hexamethyl-5,6,7,8-tetrahydronaphthalen-2-yl) ethanone; tetrahydro-4-methyl-2-(2-methylpropyl)-2H-pyran-4-ol; 2-(sec-butyl)cyclohexanone; 4,6,6,7,8,8-hexamethyl-1,3,4,6,7,8-hexahydrocyclopenta[g] isochromene; 1-phenylethyl acetate; 1-(1,2,8,8-tetramethyl-1,2,3,4,5,6,7,8-octahydronaphthalen-2-yl) ethanone; (E)-3,7-dimethylocta-2,6-dien-1-ol; (E)-oxacyclohexadec-12-en-2-one; methyl 3-oxo-2-pentylcyclopentaneacetate; 2-(1-(3,3-dimethylcyclohexyl)ethoxy)-2-methylpropyl propionate; (2 S)-ethyl 3-isopropylbicyclo[2.2.1]hept-5-ene-2-carboxylate; 2-butyl-4,4,6-trimethyl-1,3-dioxane; hexyl 2-hydroxybenzoate; 7-hydroxy-3,7-dimethyloctanal; (E)-4-(2,6,6-trimethylcyclohex-1-en-1-yl)but-3-en-2-one; 1-(2,3,8,8-tetramethyl-1,2,3,4,5,6,7,8-octahydronaphthalen-2-yl)ethanone; (4Z)-hept-4-en-2-yl 2-hydroxybenzoate; 3-(4-(tert-butyl)phenyl)-2-methylpropanal; linal oxide; 3,7-dimethylocta-1,6-dien-3-ol; (4-isopropylcyclohexyl)methanol; 6,6-dimethoxy-2,5,5-trimethylhex-2-ene; 1a,3,3,4,6,6-hexamethyl-1a,2,3,4,5,6,7,7a-octahydronaphtho[2,3-b] oxirene; 1,4-dioxacyclohexadecane-5,16-dione; cyclopentadecanone; 1,7-dioxacycloheptadecan-8-one; (E)-13-methyloxacyclopentadec-10-en-2-one; 2,4-dimethyl-2-(5,5,8,8-tetramethyl-5,6,7,8-tetrahydronaphthalen-2-yl)-1,3-dioxolane; orange essence; 4-(tert-butyl)cyclohexyl acetate; 2-phenylethanol; acetic acid (1-oxopropoxy)-, 1-(3,3-dimethylcyclohexyl)ethyl ester; 1-(3,3-dimethylcyclohexyl)ethyl acetate; (3S)-3,7-Dimethyl oct-7-en-1-ol; 2-(1-(3,3-dimethylcyclohexyl)ethoxy)-2-methylpropyl cyclopropanecarboxylate; 3-(4-isobutylphenyl)-2-methylpropanal; (E)-6,10-dimethylundeca-5,9-dien-2-yl acetate; 3,7-dimethyloctan-3-ol; and oxacyclohexadecan-2-one, wherein the perfume composition comprises less than 3% by weight of low odour ingredients having an Odour Value of less than 100, and wherein the compacted perfume composition is adapted for use as a constituent for a compacted consumer product in an amount of between 0.01 to 0.75% by weight of the compacted consumer product.

11. The process according to claim 10, further comprising the step of admixing at least one perfumery ingredient B2 belonging to none of the groups A1, A2 and B1 and having an Odour Value of 100 or more.

12. The process according to claim 10, wherein the at least three Performance Markers A1 and the at least one Performance Vehicle A2 are admixed to form a sub-composition A.

13. The process according to claim 10, wherein the at least one Performing Diluent B1 and optionally one or more other fragrance ingredients B2 are admixed to form a sub-composition B.

* * * * *